US009260686B2

(12) United States Patent
Fisher et al.

(10) Patent No.: US 9,260,686 B2
(45) Date of Patent: Feb. 16, 2016

(54) TUBULAR BIOREACTOR SYSTEM FOR USE IN BONE AND CARTILAGE TISSUE ENGINEERING

(75) Inventors: John Patrick Fisher, Kensington, MD (US); Andrew Yeatts, Silver Spring, MD (US); Elyse Geibel, Basking Ridge, NJ (US)

(73) Assignee: University of Maryland, College Park, College Park, MD (US)

( * ) Notice: Subject to any disclaimer, the term of this patent is extended or adjusted under 35 U.S.C. 154(b) by 536 days.

(21) Appl. No.: 13/253,719

(22) Filed: Oct. 5, 2011

(65) Prior Publication Data
US 2012/0122208 A1 May 17, 2012

Related U.S. Application Data

(60) Provisional application No. 61/391,303, filed on Oct. 8, 2010.

(51) Int. Cl.
- *C12N 5/0775* (2010.01)
- *C12M 3/00* (2006.01)
- *C12M 1/12* (2006.01)
- *C12M 1/34* (2006.01)

(52) U.S. Cl.
CPC ............... *C12M 25/14* (2013.01); *C12M 23/06* (2013.01); *C12M 41/00* (2013.01)

(58) Field of Classification Search
CPC ........ C12M 23/06; C12M 41/00; C12M 25/14
See application file for complete search history.

(56) References Cited

U.S. PATENT DOCUMENTS

| 4,637,990 | A * | 1/1987 | Torobin .......................... 502/10 |
| 7,767,446 | B2 | 8/2010 | Robbins et al. |
| 2007/0231305 | A1 * | 10/2007 | Noll et al. .................... 424/93.7 |
| 2009/0041825 | A1 * | 2/2009 | Kotov et al. .................. 424/423 |

OTHER PUBLICATIONS

Abbah et al. (2008) "*Osteogenic Behavior of Alginate Encapsulated Bone Marrow Stromal Cells: An in Vitro Study*," J. Mater. Sci. Mater. Med. 19:2113-2119.
Allen et al. (2003) "*Formation of Steady-State Oxygen Gradients in vitro-Application to Liver Zonation*," Biotechnol. Bioeng. 82:253-262.
Augst et al. (2006) "*Alginate Hydrogels as Biomaterials*," Macromolecular Bioscience 6:623-633.
Bacabac et al. (2005) "*Dynamic Shear Stress in Parallel-Plate Flow Chambers*," J. Biomech. 38:159-167.
Bajpai et al. (2004) "*Investigation of Swelling/Degradation Behaviour of Alginate Beads Crosslinked With Ca2+ and Ba2+ Ions*," React. Funct. Polym. 59:129-140.

(Continued)

*Primary Examiner* — Nathan Bowers
*Assistant Examiner* — Gautam Prakash
(74) *Attorney, Agent, or Firm* — William C. Schrot; AuerbachSchrot LLC

(57) ABSTRACT

A bioreactor system includes a growth chamber having an inlet, an outlet, and defining a cavity, a media reservoir is in fluid communication with the inlet, and a pump configured to perfuse a media from the reservoir into the inlet and through the growth chamber. A plurality of discrete scaffold members is packed within the growth cavity. Spaces between adjacent scaffold members define pores. The media is movable around the scaffold members and through the pores via the pump.

10 Claims, 19 Drawing Sheets

(56) References Cited

OTHER PUBLICATIONS

Bancroft et al. (2002) "*Fluid Flow Increases Mineralized Matrix Deposition in 3D Perfusion Culture of Marrow Stromal Osteoblasts in a Dose-Dependent Manner*," Proc. Natl. Acad. Sci. (U.S.A.) 99:12600-12605.

Bancroft et al. (2003) "*Design of a Flow Perfusion Bioreactor System for Bone Tissue-Engineering Applications*," Tissue Engineer. 9:549-554.

Bessa et al. (2008) "*Bone Morphogenetic Proteins in Tissue Engineering: The Road From Laboratory to Clinic, Part II (BMP Delivery)*," J. Tissue Engineer. Regen. Med. 2:81-96.

Betz et al. (2008) "*Cyclic Acetal Hydrogel System for Bone Marrow Stromal Cell Encapsulation and Osteodifferentiation*," J. Biomed. Mater. Res. Part A 86A:662-670.

Betz et al. (2009) "*Tissue Response and Orbital Floor Regeneration Using Cyclic Acetal Hydrogels*," J. Biomed. Mater. Res. 90:819-829.

Betz et al. (2010a) "*Macroporous Hydrogels Upregulate Osteogenic Signal Expression and Promote Bone Regeneration*," Biomacromolecules 11:1160-1168.

Betz et al. (2010b) "*Challenges Associated With Regeneration of Orbital Floor Bone*," Tissue Engineer. Part B Rev. 16:541-550.

Bidarra et al. (2010) "*Immobilization of Human Mesenchymal Stem Cells Within RGD-Grafted Alginate Microspheres and Assessment of Their Angiogenic Potential*," Biomacromolecules 11:1956-1964.

Bilodeau et al. (2006) "*Bioreactors for Tissue Engineering: Focus on Mechanical Constraints. A Comparative Review*," Tissue Engineer. 12:2367-2383.

Caplan (2007) "*Adult Mesenchymal Stem Cells for Tissue Engineering Versus Regenerative Medicine*," J. Cell. Physiol., 213:341-347.

Cartmell et al. (2003) "*Effects of Medium Perfusion Rate on Cell-Seeded Threedimensional Bone Constructs in vitro*," Tissue Engineer. 9:1197-1203.

Chang et al. (2004) "*Cranial repair using BMP-2 gene engineered bone marrow stromal cells*," J. Surg. Res. 119:85-91.

Chen et al. (2010) "*Macroporous Hydrogel Scaffolds and Their Characterization by Optical Coherence Tomography*," Tissue Engineer. Part C Methods 17(1):101-112.

Coates et al. (2010) "*Phenotypic Variations in Chondrocyte Subpopulations and Their Response to in Vitro Culture and External Stimuli*," Ann. Biomed. Engineer. 38:3371-3388.

Datta et al. (2006) "*in vitro Generated Extracellular Matrix and Fluid Shear Stress Synergistically Enhance 3D Osteoblastic Differentiation*," Proc. Natl. Acad. Sci. (U.S.A.) 103:2488-2493.

Engbers-Buijtenhuijs et al. (2006) "*Biological Characterization of Vascular Grafts Cultured in a Bioreactor*," Biomaterials 27:2390-2397.

Folkestad et al. (1999) "*Long-Term Sequelae After Surgery for Orbital Floor Fractures*," Otolaryngol. Head Neck Surg. 120:914-921.

Gomes et al. (2003) "*Effect of Flow Perfusion on the Osteogenic Differentiation of Bone Marrow Stromal Cells Cultured on Starchbased Three-Dimensional Scaffolds*," J. Biomed. Mater. Res. Part A 67A: 87-94.

Gomes et al. (2006) "*Bone Tissue Engineering Constructs Based on Starch Scaffolds and Bone Marrow Cells Cultured in a Flow Perfusion Bioreactor*," Adv. Mater. Forum III 514:980-986.

Grayson et al. (2008) "*Effects of Initial Seeding Density and Fluid Perfusion Rate on Formation of Tissue-Engineered Bone*," Tissue Engineer. Part A 14:1809-1821.

Grellier et al. (2009) "*Responsiveness of human bone marrow stromal cells to shear stress*," J. Tissue Engineer. Regen. Med. 3:302-309.

Guo et al. (2008) "*Osteogenic Differentiation of Human Mesenchymal Stem Cells on Chargeable Polymer-Modified Surfaces*," J. Biomed. Mater. Res. Part A 87A:903-912.

Holtorf et al. (2005) "*Flow Perfusion Culture Induces the Osteoblastic Differentiation of Marrow Stromal Cell-Scaffold Constructs in the Absence of Dexamethasone*," J. Biomed. Mater. Res. Part A 72A:326-334.

Huang et al. (2009) "*In Vitro Maturation of 'Biotube' Vascular Grafts Induced by a 2-Day Pulsatile Flow Loading*," J. Biomed. Mater. Res. Part B Appl. Biomater. 91B:320-328.

Ishaug, S.L. et al. (1997) "*Bone Formation by Three Dimensional Stromal Osteoblast Culture in Biodegradable Polymer Scaffolds*," J. Biomed. Mater. Res. 36:17-28.

Janssen et al. (2006) "*A Perfusion Bioreactor System Capable of Producing Clinically Relevant Volumes of Tissue-Engineered Bone: in Vivo Bone Formation Showing Proof of Concept*," Biomaterials 27:315-323.

Kapur et al. (2003) "*Fluid Flow Shear Stress Stimulates Human Osteoblast Proliferation and Differentiation Through Multiple Interacting and Competing Signal Transduction Pathways*," Bone 32:241-251.

Kim et al. (2010) "*Stereolithographic Bone Scaffold Design Parameters: Osteogenic Differentiation and Signal Expression*," Tissue Engineer. Part B Rev 16:523-542.

Kreke et al. (2005) "*Fluid Flow Stimulates Expression of Osteopontin and Bone Sialoprotein by Bone Marrow Stromal Cells in a Temporally Dependent Manner*," Bone 36:1047-1055.

Kuo et al. (2001) "*Ionically Crosslinked Alginate Hydrogels as Scaffolds for Tissue Engineering: Part 1. Structure, Gelation Rate and Mechanical Properties*," Biomaterials 22:511-521.

Kurosawa et al. (1989) "*Diffusivity in Gel Beads Containing Viable Cells*," Biotechnol. Bioengineer. 34:926-932.

Lee et al. (2000) "*Controlling Mechanical and Swelling Properties of Alginate Hydrogels Independently by Cross-Linker Type and Cross-Linking Density*," Macromolecules 33:4291-4294.

Leung et al. (2010) "*A Modular Approach to Cardiac Tissue Engineering*," Tissue Engineer. Part A 16:3207-3218.

Li et al. (2009) "*Effects of Flow Shear Stress and Mass Transport on the Construction of a Large-Scale Tissue Engineered Bone in a Perfusion Bioreactor*," Tissue Engineer. Part A 15:2773-2786.

Malda et al. (2007) "*The Roles of Hypoxia in the in Vitro Engineering of Tissues*," Tissue Engineering 13:2153-2162.

Mancini et al. (1999) "*Mechanical Properties of Alginate Gels: Empirical Characterization*," J. Food Engineer. 39:369-378.

Martin et al. (2004) "*The Role of Bioreactors in Tissue Engineering*," Trends Biotechnol. 22:80-86.

Mauney et al. (2005) "*Role of Adult Mesenchymal Stem Cells in Bone Tissue-Engineering Applications: Current Status and Future Prospects*," Tissue Engineer. 11:787-808.

McGuigan et al. (2006) "*Vascularized Organoid Engineered by Modular Assembly Enables Blood Perfusion*," Proc. Natl. Acad. Sci. (U.S.A.) 103:11461-11466.

Meinel et al. (2004) "*Bone Tissue Engineering Using Human Mesenchymal Stem Cells: Effects of Scaffold Material and Medium Flow*," Ann. Biomed. Engineer. 32:112-122.

Meuwly et al. (2007) "*Packed-Bed Bioreactors for Mammalian Cell Culture: Bioprocess and Biomedical Applications*," Biotechnol Adv 25:45-56.

Moe et al. (1993) "*Swelling of Covalently Cross-Linked Alginate Gels—Influence of Ionic Solutes and Nonpolar-Solvents*," Macromolecules 26:3589-3597.

Palmiero et al. (2010) "*Engineered Dermal Equivalent Tissue in Vitro by Assembly of Microtissue Precursors*," Acta Biomater. 6:2548-2553.

Patel et al. (2010) "*Cyclic Acetal Hydroxyapatite Nanocomposites for Orbital Bone Regeneration*," Tissue Engineer. Part A 16:55-67.

Peng et al. (1996) "*Determination of specific oxygen uptake rates in human hematopoietic cultures and implications for bioreactor design*," Ann Biomed Engineer. 24:373-381.

Porter et al. (2007) "*Noninvasive Image Analysis of 3D Construct Mineralization in a Perfusion Bioreactor*," Biomaterials 28:2525-2533.

Portner et al. (2005) "*Bioreactor Design for Tissue Engineering*," J. Biosci. Bioengineer. 100:235-245.

Rinna et al. (2005) "*Orbital Floor Restoration*," J. Craniofac. Surg. 16:968-972.

Rowley et al. (1999) "*Alginate Hydrogels as Synthetic Extracellular Matrix Materials*," Biomaterials 20:45-53.

(56) References Cited

OTHER PUBLICATIONS

Sikavitsas et al. (2003) "*Mineralized Matrix Deposition by Marrow Stromal Osteoblasts in 3D Perfusion Culture Increases With Increasing Fluid Shear Forces*," Proc. Natl. Acad. Sci. (U.S.A.) 100:14683-14688.

Sikavitsas et al. (2005) "*Flow Perfusion Enhances the Calcified Matrix Deposition of Marrow Stromal Cells in Biodegradable Nonwoven Fiber Mesh Scaffolds*," Ann. Biomed. Engineer. 33:63-70.

Stiehler et al. (2009) "*Effect of Dynamic 3-D Culture on Proliferation, Distribution, and Osteogenic Differentiation of Human Mesenchymal Stem Cells*," J. Biomed. Mater. Res. Part a 89A:96-107.

Thompson et al. (2009) "*Osteogenic Differentiation of Bone Marrow Stromal Cells Induced by Coculture With Chondrocytes Encapsulated in Threedimensional Matrices*," Tissue Engineer. Part A 15:1181-1191.

Ueng. et al. (2007) "*Development of a Biodegradable Alginate Carrier System for Antibiotics and Bone Cells*," J. Orthop. Res. 25:62-72.

van den Dolder et al. (2003) "*Flow Perfusion Culture of Marrow Stromal Osteoblasts in Titanium Fiber Mesh*," J. Biomed. Mater. Res. Part A 64A:235-241.

Volkmer et al. (2008) "*Hypoxia in Static and Dynamic 3D Culture Systems for Tissue Engineering of Bone*," Tissue Engineer. Part A 14:1331-1343.

Wang et al. (2003) "*Evaluation of Sodium Alginate for Bone Marrow Cell Tissue Engineering*," Biomaterials 24:3475-3481.

Wang et al. (2009) "*Regulation of Adult Human Mesenchymal Stem Cells Into Osteogenic and Chondrogenic Lineages by Different Bioreactor Systems*," J. Biomed. Mater. Res. Part A 88A:935-946.

Williams et al. (2005a) "*Perfusion Bioreactor for Small Diameter Tissue-Engineered Arteries*," Tissue Engineer. 10:930-944.

Williams et al. (2005b) "*Endothelial Cell-Smooth Muscle Cell Co-Culture in a Perfusion Bioreactor System*," Ann. Biomed. Engineer. 33:920-928.

Yeatts et al. (2011) "*Tubular Perfusion System for the Long-Term Dynamic Culture of Human Mesenchymal Stem Cells*," Tissue Engineer. Part C Methods 17:337-348.

Yoon et al. (2006) "*Chondrocyte Signaling and Artificial Matrices for Articular Cartilage Engineering*," Adv. Exp. Med. Biol. 585:67-86.

Yoon et al. (2007) "*Effect of Construct Properties on Encapsulated Chondrocyte Expression of Insulin-Like Growth Factor-1*," Biomaterials 28:299-306.

Yoon et al. (2008) "*Effects of Exogenous IGF-1 Delivery on the Early Expression of IGF-1 Signaling Molecules by Alginate Embedded Chondrocytes*," Tissue Engineer. Part A 14:1263-1273.

Yoon et al. (2009) "*Addition of Hyaluronic Acid to Alginate Embedded Chondrocytes Interferes with Insulin-like Growth Factor-1 Signaling in Vitro and in Vivo*," Tissue Engineering Part A 15:3449-3459.

Yu et al. (2004) "*Bioreactor-Based Bone Tissue Engineering: The Influence of Dynamic Flow on Osteoblast Phenotypic Expression and Matrix Mineralization*," Proc. Natl. Acad. Sci. (U.S.A.) 101:11203-11208.

Zhao et al. (2005) "*Effects of Oxygen Transport on 3-D Human Mesenchymal Stem Cell Metabolic Activity in Perfusion and Static Cultures: Experiments and Mathematical Model*," Biotechnol. Prog. 21:1269-1280.

Reissis et al. (2013) "*The effect of temperature on the viability of human mesenchymal stem cells*," Stem Cell Research & Therapy 4:139 (11 pages).

\* cited by examiner

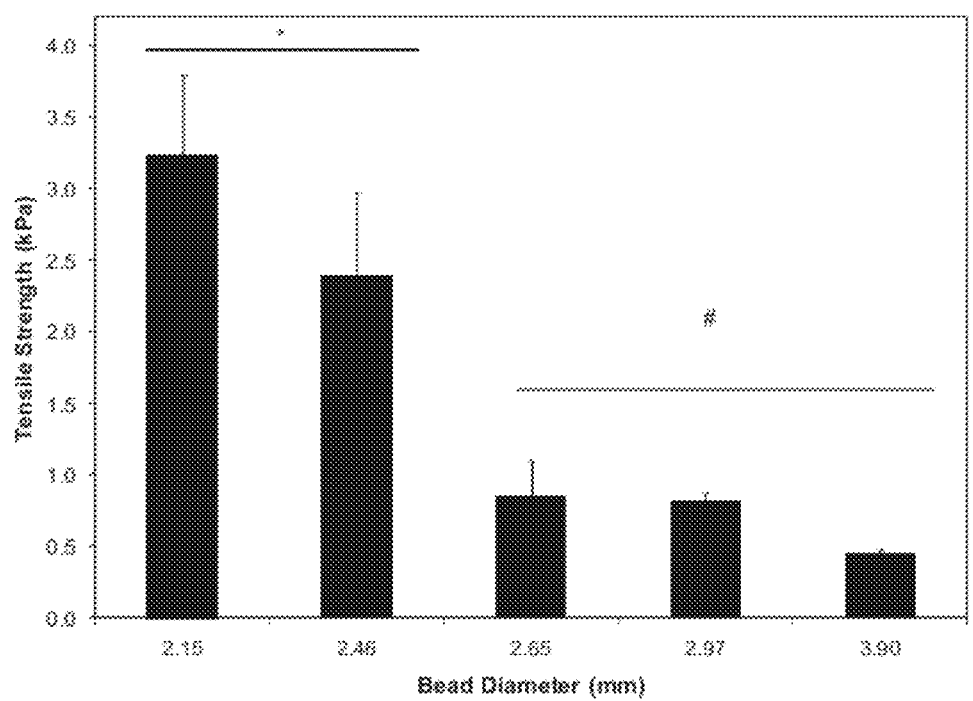

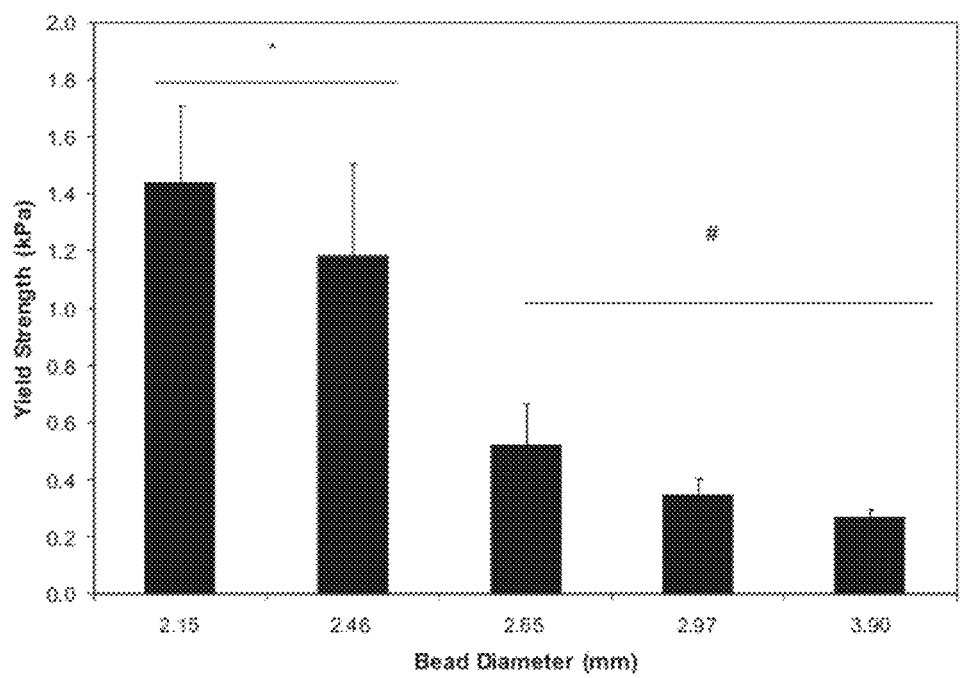

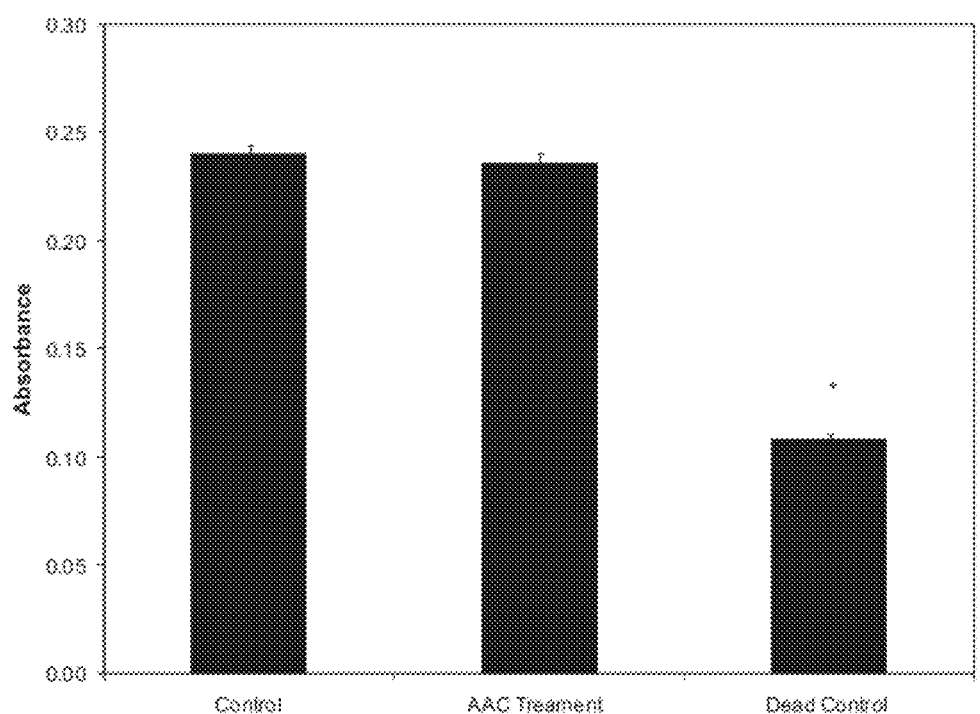

Figure 9
(a)
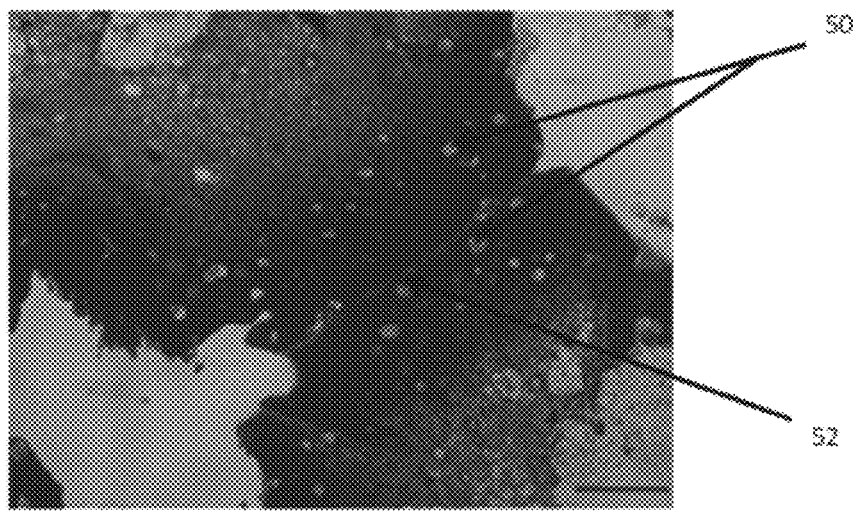
(b)
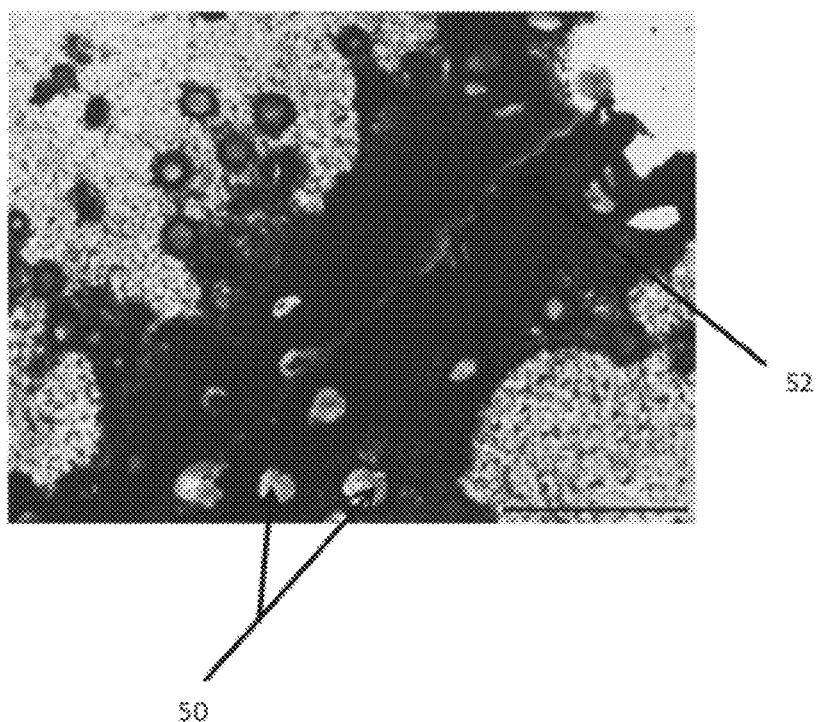

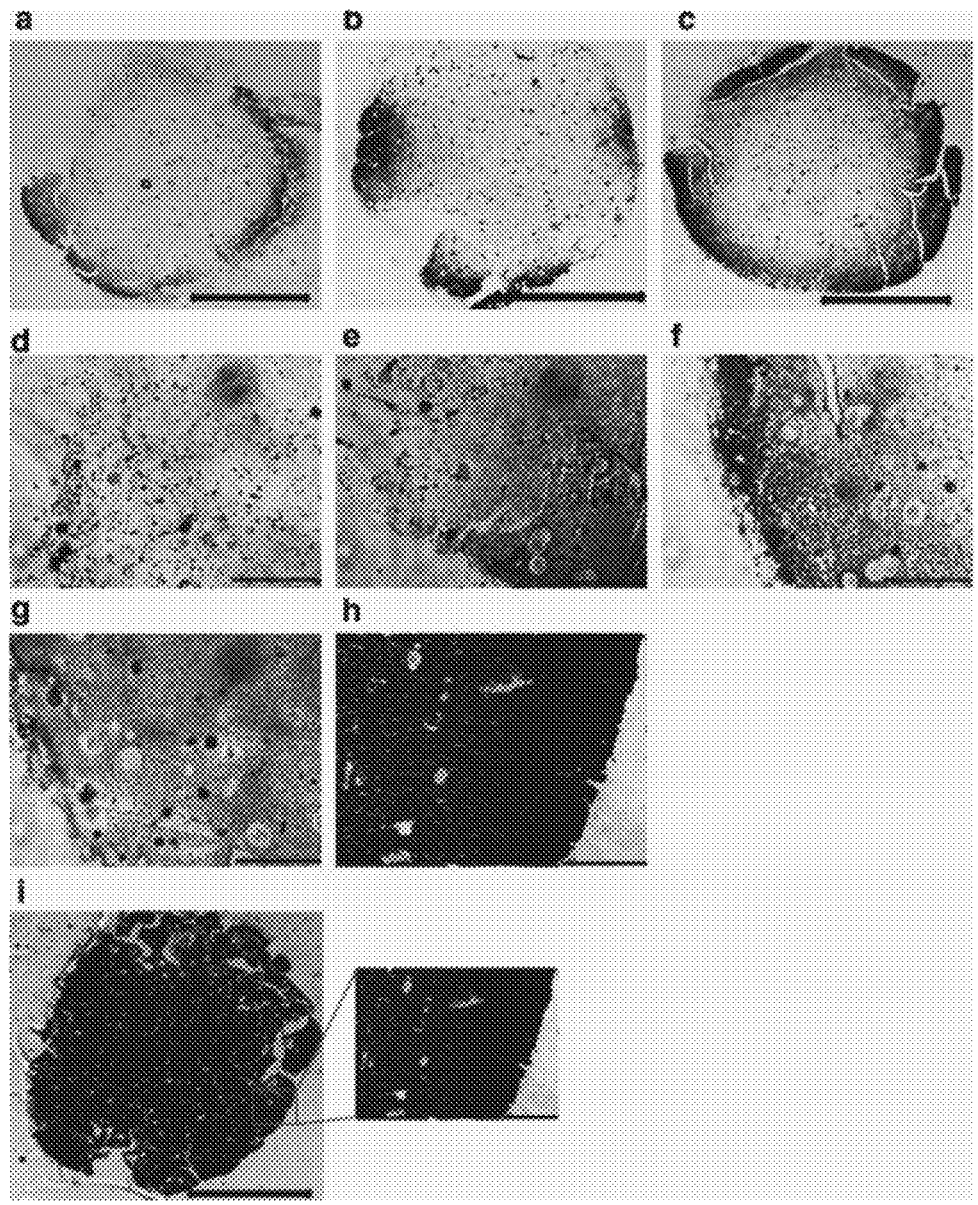

TUBULAR BIOREACTOR SYSTEM FOR USE IN BONE AND CARTILAGE TISSUE ENGINEERING

CROSS-REFERENCE TO RELATED APPLICATIONS

This application is based on U.S. Patent Application Ser. No. 61/391,303, filed Oct. 8, 2010, which application is incorporated herein by reference in its entirety and to which priority is claimed.

STATEMENT REGARDING FEDERALLY SPONSORED RESEARCH OR DEVELOPMENT

This invention was made with government support under BES0448684 awarded by The National Science Foundation. The government has certain rights in this invention.

FIELD OF THE INVENTION

The present invention relates to a bioreactor system, a method of culturing cells, and engineered tissue aggregated from discrete scaffold members or elements that are cultured individually prior to aggregation.

BACKGROUND OF THE INVENTION

In vitro culture techniques have limitations that must be overcome to increase the feasibility of cell-based tissue engineering strategies. A limitation in static culture is insufficient transport of oxygen and other nutrients to regions more than a few hundred microns from the scaffold surface, which leads to nonhomogenous cell distribution and extracellular matrix production. See Ishaug, S. L. et al. (1997) "*Bone formation by three dimensional stromal osteoblast culture in biodegradable polymer scaffolds,*" J Biomed Mater Res 36:17; Yu et al. (2004) "*Bioreactor-based bone tissue engineering: the influence of dynamic flow on osteoblast phenotypic expression and matrix mineralization,*" Proc Natl Acad Sci USA 101: 11203; Gomes et al. (2003) "*Effect of flow perfusion on the osteogenic differentiation of bone marrow stromal cells cultured on starchbased three-dimensional scaffolds,*" J Biomed Mater Res Part A 67A: 87; Volkmer et al. (2008) "*Hypoxia in static and dynamic 3D culture systems for tissue engineering of bone,*" Tissue Eng Part A 14:1331; and Martin et al. (2004) "*The role of bioreactors in tissue engineering,*" Trends Biotechnol 22:80. Conventional bioreactor systems attempt to overcome these limitations by increasing nutrient transfer to cells via dynamic culture. Further, mechanical stimulation through fluid shear stresses has been shown to be influential on bone differentiation and mineralization. See Bilodeau et al. (2006) "*Bioreactors for tissue engineering: focus on mechanical constraints. A comparative review,*" Tissue Eng 12:2367; Bancroft et al. (2003) "*Design of a flow perfusion bioreactor system for bone tissue-engineering applications,*" Tissue Eng 9:549; Bancroft et al. (2002) "*Fluid flow increases mineralized matrix deposition in 3D perfusion culture of marrow stromal osteoblasts in a dose-dependent manner,*" Proc Natl Acad Sci USA 99:12600.

Another significant challenge in the implementation of cell based tissue engineering strategies remains the inability to successfully culture large constructs in vitro. One approach to overcoming this difficulty is a bottom up approach to creating a tissue engineering construct. A unitary polymer scaffold is constructed in its final shape and seeded with cells. The cells are then cultured in vitro to allow for proliferation and matrix deposition throughout the scaffold. However, such bottom up approaches are limited by the scaffold size and cell density that will allow for homogenous growth and matrix production throughout the scaffold. For example, central oxygen concentration of cells cultured in scaffolds 9 mm by 5 mm were shown to drop to 0% after just five days of culture. Bioreactor culture mitigate this effect. However, central oxygen concentration of the same constructs cultured in a conventional perfusion bioreactor were only 4%.

Some previous studies focus on bioreactor systems as a means to culture cells for bone tissue engineering purposes. See Meinel et al. (2004) "*Bone tissue engineering using human mesenchymal stem cells: effects of scaffold material and medium flow,*" Ann Biomed Eng 32:112; Sikavitsas et al. (2003) "*Mineralized matrix deposition by marrow stromal osteoblasts in 3D perfusion culture increases with increasing fluid shear forces,*" Proc Natl Acad Sci USA 100:14683; Sikavitsas et al. (2005) "*Flow perfusion enhances the calcified matrix deposition of marrow stromal cells in biodegradable nonwoven fiber mesh scaffolds,*" Ann Biomed Eng 33:63; Sikavitsas et al. (2002) "*Formation of three-dimensional cell/polymer constructs for bone tissue engineering in a spinner flask and a rotating wall vessel bioreactor,*" J Biomed Mater Res 62:136; van den Dolder et al. (2003) "*Flow perfusion culture of marrow stromal osteoblasts in titanium fiber mesh,*" J Biomed Mater Res Part A 64A:235; Grayson et al. (2008) "*Effects of initial seeding density and fluid perfusion rate on formation of tissue-engineered bone,*" Tissue Eng Part A 14:1809; Janssen et al. (2006) "*A perfusion bioreactor system capable of producing clinically relevant volumes of tissue-engineered bone: in vivo bone formation showing proof of concept,*" Biomaterials 27:315.

Several different types of bioreactor systems have been investigated, including spinner flasks (Stiehler et al. (2009) "*Effect of dynamic 3-D culture on proliferation, distribution, and osteogenic differentiation of human mesenchymal stem cells,*" J Biomed Mater Res Part A 89A:96), rotating wall bioreactors (Wang et al. (2009) "*Regulation of adult human mesenchymal stem cells into osteogenic and chondrogenic lineages by different bioreactor systems,*" J Biomed Mater Res Part A 88A:935), and perfusion systems (Gomes et al. (2006) "*Bone tissue engineering constructs based on starch scaffolds and bone marrow cells cultured in a flow perfusion bioreactor,*" Adv Mater Forum III 514:980; Holtorf et al. (2005) "*Flow perfusion culture induces the osteoblastic differentiation of marrow stromal cell-scaffold constructs in the absence of dexamethasone,*" J Biomed Mater Res Part A 72A:326; Datta et al. (2006) "*In vitro generated extracellular matrix and fluid shear stress synergistically enhance 3D osteoblastic differentiation,*" Proc Natl Acad Sci USA 103: 2488). Spinner flask and rotating wall bioreactor systems are effective at creating a homogenous media solution on the exterior of the scaffold, but do not effectively perfuse media into the scaffold.

Perfusion systems have been demonstrated to perfuse media throughout the scaffold and have been shown to upregulate osteoblastic markers and increase calcium deposition. In a study utilizing a perfusion bioreactor, flow rate was shown to increase both the calcium matrix deposition and the rate of late osteoblastic differentiation as shown by osteopontin (OPN) expression. See Bancroft et al. (2002), supra, Proc Natl Acad Sci USA 99:12600. Although conventional perfusion systems typically enhance the flow of media to the center of the scaffold, they require custom-made parts and specific scaffold design to successfully perfuse media into the scaffold, making them difficult to fabricate and use.

SUMMARY OF THE INVENTION

The present invention relates to a bioreactor system, a method of culturing cells, and engineered tissue aggregated from discrete scaffold members or elements (e.g., alginate beads), which are cultured individually prior to aggregation. This allows for the in vitro development of tissue engineering constructs on size scales not possible with conventional culture methods.

The present invention also relates to a bioreactor system including a growth chamber having an inlet and an outlet and defining a cavity, a media reservoir, and a pump. The media reservoir is in fluid communication with the inlet of the growth chamber. The pump is configured to perfuse a media from the media reservoir into the inlet and through the growth chamber. A plurality of discrete scaffold members are disposed within the cavity of the growth chamber. The growth chamber may have a generally tubular configuration, so that the plurality of discrete scaffold members packed therein collectively also have a generally tubular configuration. Spaces between adjacent scaffold members define pores. The media is movable around the scaffold members and through the pores via the pump.

In one embodiment, each of the discrete scaffold members has a generally bead-shaped configuration. In one implementation, each of the scaffold members has a diameter of between about 2 mm and about 4 mm. In one implementation, the discrete scaffold members comprise alginate. In other implementations, the discrete scaffold members comprise poly(caprolactone) (PCL), or poly(1-lactic acid) (PLLA), or some other biomaterial that supports cell adhesion and viability. Each of the discrete scaffold members includes a structure containing or supporting a cell population. For example, the cell population may be encapsulated within the scaffold, or alternatively seeded or disposed on the surface of the scaffold and permitted to migrate throughout the scaffold. In one implementation, the cell population comprises human mesenchymal stem cells. The media is perfusable through the outer scaffold surface or interface and into an interior or inner portion of the discrete scaffold members, thereby permitting the diffusion of molecules such as the influx of oxygen, nutrients, etc. essential for cell metabolism and growth, and the outward diffusion of waste products.

In one embodiment, the system includes a first screen proximate the inlet and a second screen proximate the outlet. The plurality of discrete scaffold members are tightly packed within the growth chamber and maintained therein between the first and second screens. In one implementation, the media is perfused through the growth chamber via a peristaltic pump.

In one embodiment, the media is movable through the growth chamber at a flow rate of between about 0.1 mL/minute and about 47.0 mL/minute. In one implementation, the media is movable through the growth chamber at a flow rate of at least about 10 mL/minute. In another implementation, the media is movable through the growth chamber at a flow rate of between about 20 mL/minute and about 40 mL/minute. In one embodiment, the media imparts shear stresses of between about 0.5 dynes/$cm^2$ and about 3.0 dynes/$cm^2$ proximate to surfaces of the discrete scaffold members.

The present invention also relates to a bioreactor system comprising a tubular growth chamber and a plurality of discrete scaffold members. The growth chamber includes an inlet and an outlet, and defines a cavity. The scaffold members are packed within the cavity. Each of the scaffold members comprises a hydrogel encapsulating or containing a cell population, such as a population of human mesenchymal stem cells. In one embodiment, each of the scaffold members has a generally bead-shaped configuration having a diameter of between about 2 mm and about 4 mm. The scaffold members may be formed from alginate, PCL, PLLA, or some other biomaterial that supports cell adhesion and viability.

The present invention also relates to a method of culturing cells comprising the steps of: providing a plurality of discrete scaffold members, each of the scaffold members encapsulating or containing a cell population; packing the scaffold members into a growth chamber so that spaces between adjacent scaffold members define pores; and perfusing media around the scaffold members and through the pores within the growth chamber via a pump, thereby culturing the cell populations.

In one embodiment, the disclosed method comprises the further step of dissolving the scaffold members so that the remaining cell populations define an extracellular matrix or engineered tissue construct. In one implementation, the cell population is human mesenchymal stem cells.

BRIEF DESCRIPTION OF THE DRAWINGS

FIGS. 5A, 5B and 5C are graphs illustrating mechanical properties of aggregated alginate construct including Young's Modulus (FIG. 5A), tensile strength (FIG. 5B) and yield strength (FIG. 5C). Bead groups having diameters of 2.15 mm and 2.46 mm are statistically greater than other bead diameter groups, and statistically similar to each other. The symbols (*, #) indicate statistical significance ($p<0.05$).

FIG. 6 is a graph illustrating metabolic activity of cells in alginate beads in control media, AAC treatment, and dead control. Dead control is significantly lower than control bead and AAC treatment, which are statistically similar. The symbol (*) indicates statistical significance ($p<0.05$).

FIG. 9 (plates a and b) are von Kossa staining images of AAC formed after 21 days of in vitro TPS culture of individual alginate beads in osteogenic media at 20× objective (shown in plate (a)) and 40× objective (shown in plate (b)). The images show cells (50) at or proximate to the juncture (52) or exterior surfaces of two adjacent beads in the AAC surrounded by calcium deposits (dark black). The scale bars in the lower right corner of each plate represents 100 μm.

Figure 1:
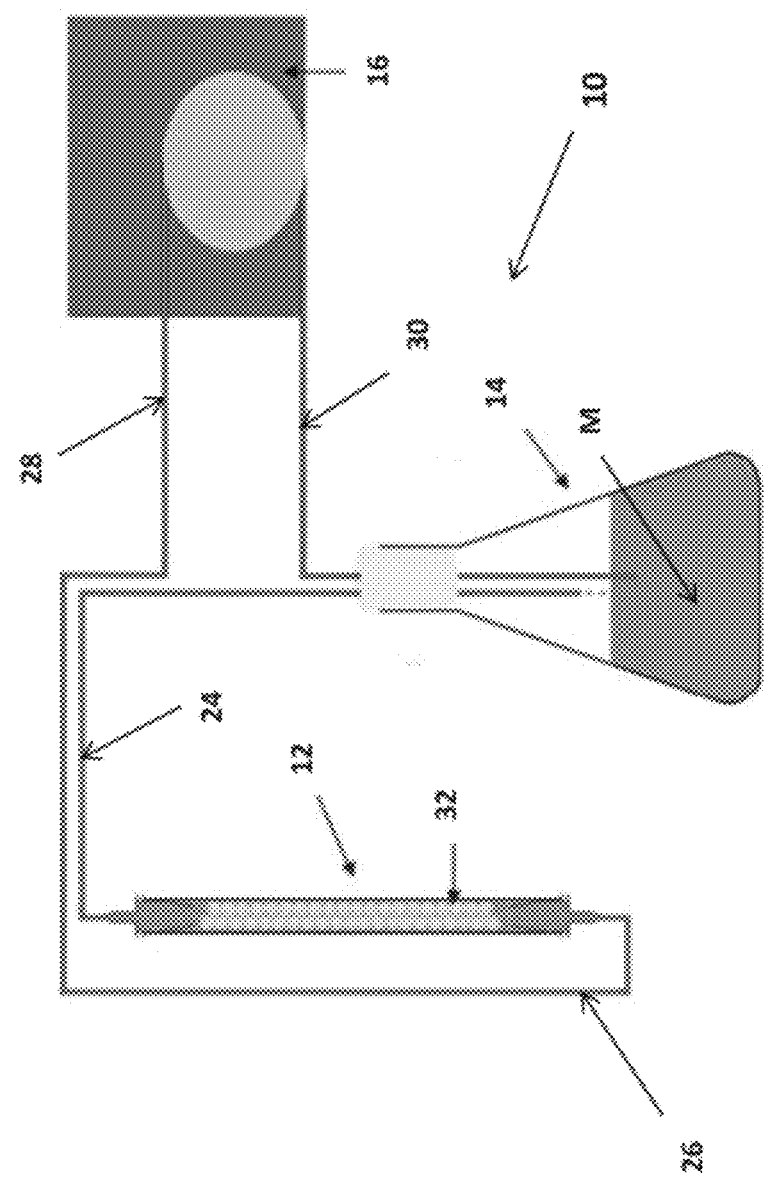
FIG. 1 illustrates a schematic diagram of a bioreactor system according to an embodiment of the present invention.

Beads were then dissolved for 30 min in 0.025-Methyl-diaminetetraacetic acid. Images of scaffolds cultured in static control media are shown at plate (d), static osteogenic media at plate (e), and bioreactor culture (3 mL/min) at plate (f) after 28 days and 30 min in 0.025M thyldiaminetetraacetic acid. Alginate scaffold can no longer be observed in control media sample. In the osteogenic control group, small macroscopic formations remain. In the bioreactor group, larger more intact cell scaffold constructs are observed having diameters of about 4 mm. The scale bars at the lower right corners of each plate represent 5 mm.

FIG. 17 (plates a, b, c, d, e, f, g, h, and i) are von Kossa staining images of alginate beads after 14 days of culture in static osteogenic culture (plates (a) and (d)), 3 mL/min bioreactor culture (plates (b) and (e)), and 10 mL/min bioreactor culture (plates (c) and (f)) at 2.5× objective (plates (a)-(c)) and 40× objective (plates (d)-(f)). Calcium deposits (shown in black) appear to be confined to the perimeter of the bead in all groups, but darker in the bioreactor groups, with the greatest amount of deposition observed in the mL/min bioreactor group. After 28 days of culture, von Kossa staining reveals 3 mL/min bioreactor culture (plate (h)) and shows darker staining indicating increased calcium deposits compared to the static osteogenic control (plate (g)). Beads did not remain intact in the 10 mL/min group and von Kossa staining was not completed on day 28. The scale bars in the lower right corner of plates (a)-(c) represent 1000 nm. The scale bars in the lower right corner of plates (d)-(h) represent 100 nm. The exploded boxed portion of plate (i) denotes the size and approximate location of all 40× objective images (plates (d)-(f)) in relation to the entire bead. The image of plate (i) is of 3 mL bioreactor groups after 28 days at 2.5× objective with the scale bar representing 1000 nm, and 40× objective shown in the boxed exploded portion (to the right of plate (i)) with the scale bar representing 100 nm.

DETAILED DESCRIPTION OF THE INVENTION

The present invention is directed to a bioreactor system, sometimes referred to herein as a tubular perfusion system (TPS) bioreactor, which enhances nutrient transport and cultures cell populations in three-dimensional scaffolds. The system utilizes an elegant design which creates a more effective environment for cell culture. In one implementation, the bioreactor system involves the culture of human mesenchymal stem cells (hMSCs), which are encapsulated in, or contained within and/or on the surface of, alginate scaffolds or beads. The TPS system includes a plurality of the discrete alginate scaffolds, which are tightly packed in a tubular growth chamber. Media is pumped through the growth chamber from a reservoir via a peristaltic pump.

The disclosed TPS bioreactor system has been shown to support the growth and osteoblastic differentiation of hMSCs as well as enhance late osteoblastic differentiation and calcium matrix production. hMSCs are utilized as a promising cell source for both bone and cartilage tissue engineering, as they can be isolated from the bone marrow and readily differentiated into both osteoblasts and chondrocytes. See Caplan, A. (2007) "*Adult mesenchymal stem cells for tissue engineering versus regenerative medicine,*" Journal of Cellular Physiology, 213:341-7. The hMSCs are encapsulated in alginate, a natural biomaterial derived from algae that is frequently utilized in cartilage tissue engineering (Augst et al. (2006) "*Alginate hydrogels as biomaterials,*" Macromolecular Bioscience 6:623-33; Yoon et al. (2009) "*Addition of Hyaluronic Acid to Alginate Embedded Chondrocytes Interferes with Insulin-like Growth Factor-1 Signaling In Vitro and In Vivo,*" Tissue Engineering Part A 15:3449-59; Yoon et al. (2008) "*Effects of exogenous IGF-1 delivery on the early expression of IGF-1 signaling molecules by alginate embedded chondrocytes,*" Tissue Eng Part A 14:1263-73; Yoon et al. (2007) "*Effect of construct properties on encapsulated chondrocyte expression of insulin-like growth factor-1,*" Biomaterials 28:299-306; Thompson et al. (2009) "*Osteogenic differentiation of bone marrow stromal cells induced by coculture with chondrocytes encapsulated in three-dimensional matrices,*" Tissue Eng Part A 15:1181), as well as some bone tissue engineering applications (Bidarra et al. (2010) "*Immobilization of Human Mesenchymal Stem Cells within RGD-Grafted Alginate Microspheres and Assessment of Their Angiogenic Potential,*" Biomacromolecules 11:1956-64; Chang et al. (2004) "*Cranial repair using BMP-2 gene engineered bone marrow stromal cells,*" Journal of Surgical Research 119:85-91; Ueng et al. (2007) "*Development of a biodegradable alginate carrier system for antibiotics and bone cells,*" J Orthop Res 25:62-72; Wang et al. (2003) "*Evaluation of sodium alginate for bone marrow cell tissue engineering,*" Biomaterials 24:3475-81).

Alginate may be used as a scaffold because of its ability to be dissolved with a calcium chelating agent, and because of the ease of which it can be formed into spherical scaffolds. Alginate is composed of mannuronic acid and guluronic acid chains. When a divalent ion such as calcium is added to an alginate solution, the calcium binds between guluronic acid blocks of the alginate chain ionically crosslinking the alginate chains and gelling the alginate solution. See Rowley et al. (1999) "*Alginate hydrogels as synthetic extracellular matrix materials,*" Biomaterials 20:45-53. Thus, cells can be easily encapsulated in or disposed on an alginate hydrogel by mixing an alginate cell solution and adding the solution dropwise via a needle into a calcium chloride solution. The size of the alginate beads may be selectively controlled by changing the size of the needle. The beads can then be dissolved through the addition of a calcium chelating agent such as ethyldiaminetetraacetic acid (EDTA) which sequesters the crosslinking calcium ions. This makes alginate advantageous for in vitro experimentation as cells can easily be removed and analyzed.

Alginate has previously been shown to support proliferation and osteoblastic differentiation of marrow stromal cells. Abbah et al. (2008) "*Osteogenic behavior of alginate encapsulated bone marrow stromal cells: an in vitro study,*" J. Mater Sci Mater Med 19:2113. In addition, alginate has been used for bone tissue engineering purposes, including supporting two-dimensional (2D) osteoblastic differentiation of marrow stromal cells, delivery of bone morphogenetic protein-2 (BMP-2)-transfected bone marrow stromal cells, the delivery of antibiotics and MSCs to bone injury sites, and mineralization of hMSCs in arginine-glycine-aspartic acid (RGD)-modified microspheres. Chang et al. (2004) "*Cranial repair using BMP-2 gene engineered bone marrow stromal cells,*" J Surg Res 119:85; Wang et al. (2003) "*Evaluation of sodium alginate for bone marrow cell tissue engineering,*" Biomaterials 24:3475; Ueng et al. (2007) "*Development of a biodegradable alginate carrier system for antibiotics and bone cells,*" J Orthop Res 25:62; Bidarra et al. (2010) "*Immobilization of human mesenchymal stem cells within RGD-grafted alginate microspheres and assessment of their angiogenic potential,*" Biomacromolecules 11:1956. MSCs are used as a promising cell source for bone tissue engineering. Mauney et al. (2005) "*Role of adult mesenchymal stem cells in bone tissue-engineering applications: current status and future prospects,*" Tissue Eng 11:787.

It should be understood that the present invention is not limited to scaffold members comprising alginate. In other implementations, the discrete scaffold members comprise PCL, or PLLA, or some other biomaterial that supports cell adhesion and viability.

A bioreactor system 10 according to an embodiment of the present invention is illustrated in FIG. 1. The bioreactor system 10 includes a growth chamber 12, a media reservoir 14 in fluid communication with the growth chamber 12, and a pump 16 configured to perfuse media M from the reservoir 14 and through the growth chamber 12. In one implementation, the pump 16 is a peristaltic pump. It should be understood that the system 10 may include multiple growth chambers and/or reservoirs, and thus the present invention is not limited to the exemplary system configuration illustrated in FIG. 1.

Figure 2:
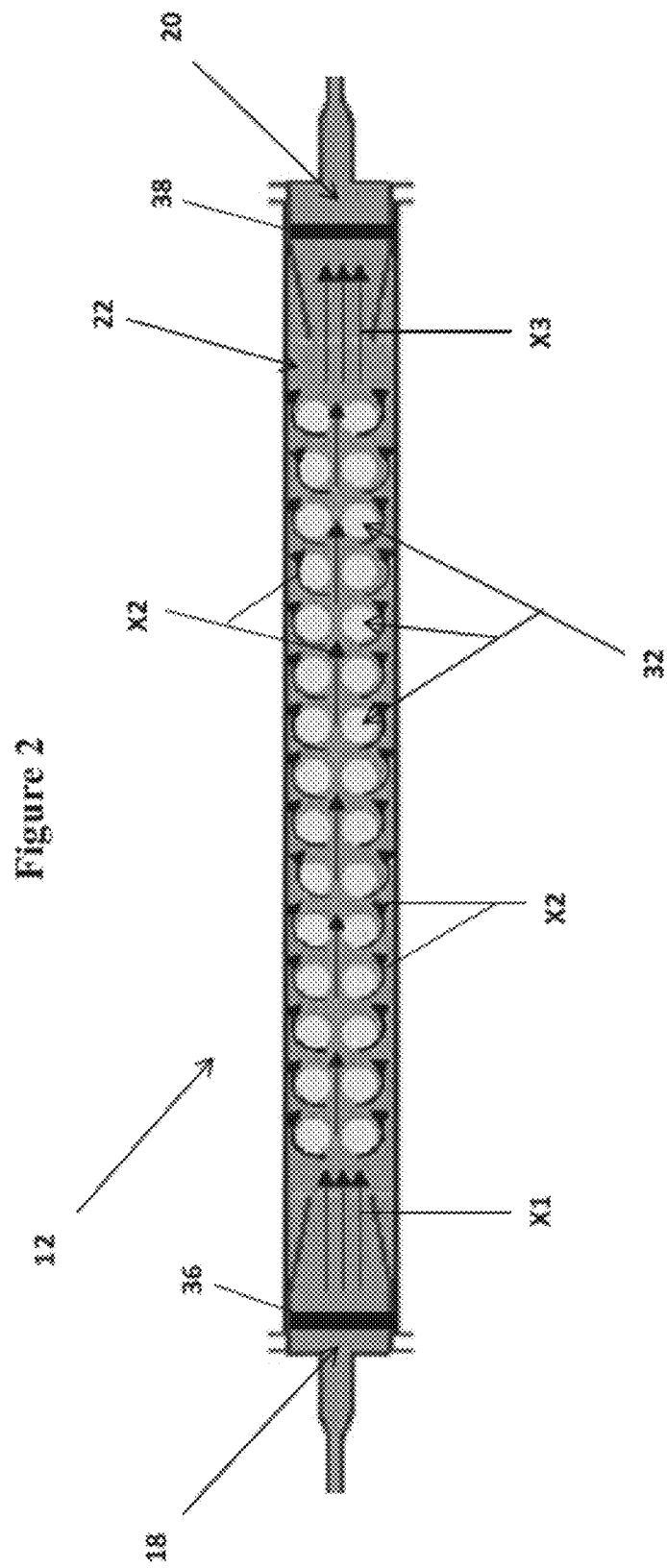
FIG. 2 illustrates an exploded view of a growth chamber of the bioreactor system of FIG. 1, showing a cavity of the growth chamber packed with a plurality of discrete scaffold members comprised of alginate beads.

Referring to FIGS. 1 and 2, the growth chamber 12 includes an inlet 18 and an outlet 20, and defines a cavity 22. The media reservoir 14 is in fluid communication with the inlet 18 of the growth chamber 12 via tubing 24, and the outlet 20 is in fluid communication with the media reservoir 14 via tubing 26. The pump 16 is intermediate a first portion 28 of the tubing 26 and a second portion 30 of the tubing 26, between the outlet 20 and the media reservoir 14. Thus, media M is circulated through the growth chamber 12 at a selected flow rate via the pump 16.

A plurality of discrete scaffold members 32 are disposed within the cavity 22 of the growth chamber 12. Spaces between adjacent scaffold members 32 define pores, gaps or channels. A first screen 36 is disposed within the growth chamber 12 and proximate to the inlet 18. A second screen 38 is disposed within the growth chamber 12 and proximate to the outlet 20. The plurality of discrete scaffold members 32 are tightly packed within the growth chamber 12 and maintained therein and between the first and second screens 36, 38.

Figure 3:
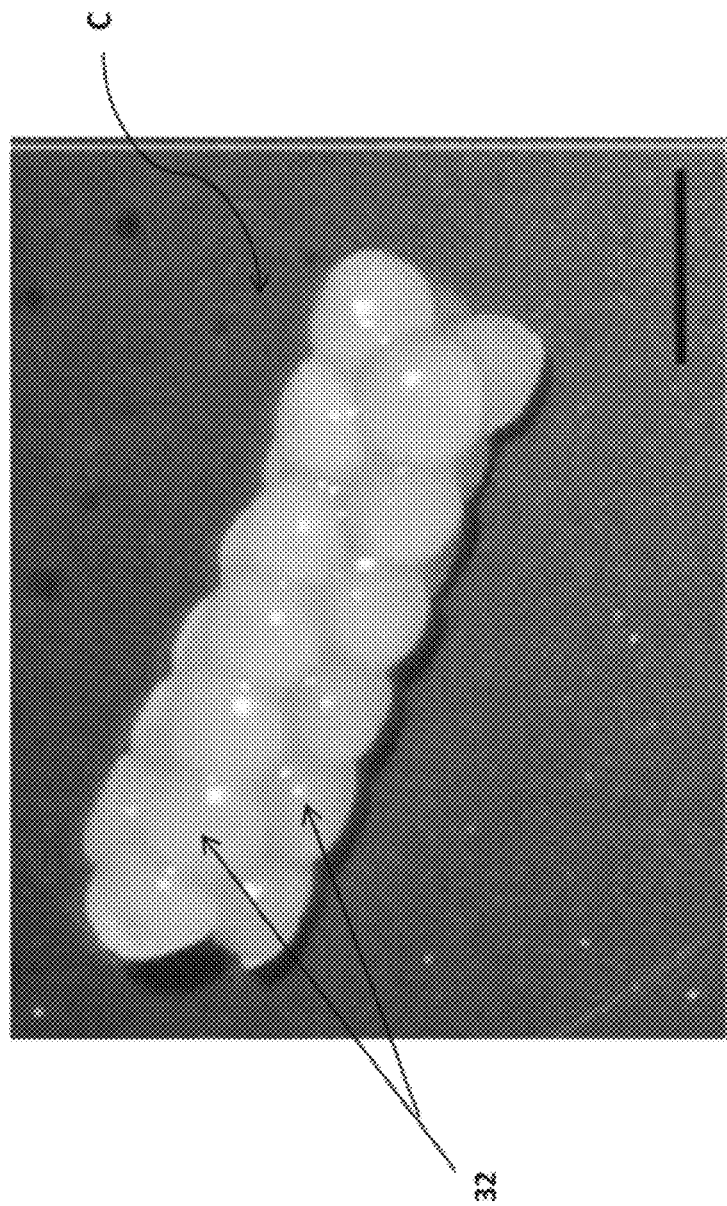
FIG. 3 is a perspective image of an aggregated alginate construct, with a scale bar in the lower right corner representing 5 mm. The construct is easily movable and manipulated due to the simplicity and integrity of the construct.
Figure 4:
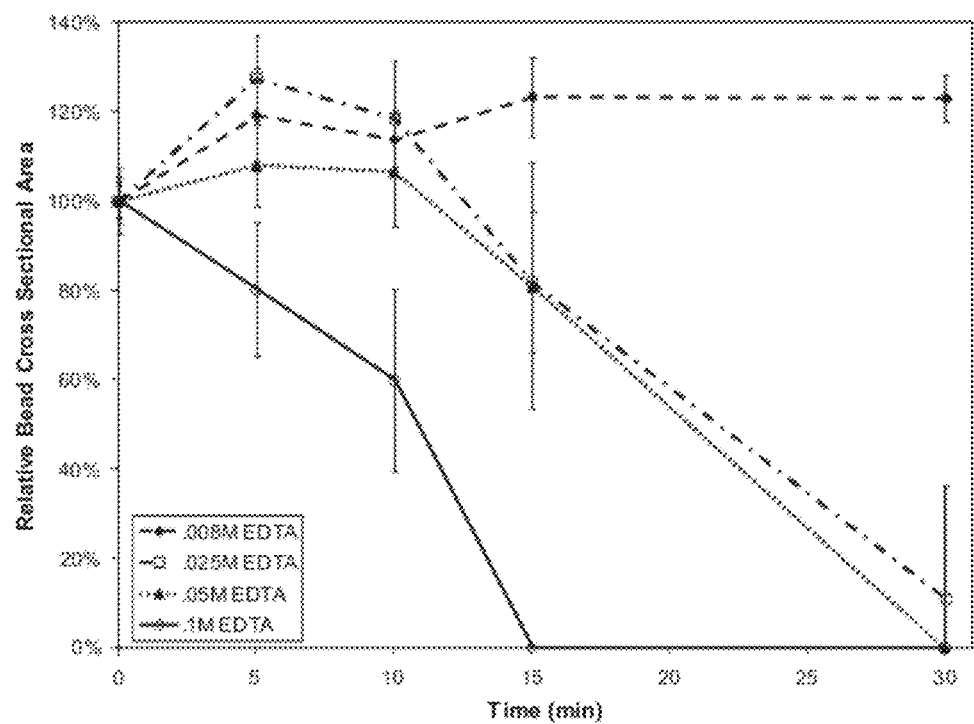
FIG. 4 is a graph illustrating the dissolution rate of alginate beads at varying EDTA concentrations of 1.8 mL/min flow rate. Bead sizes are reported as cross-sectional areas in relation to initial area.

Referring to FIGS. 2, 3 and 4, in one implementation, each of the discrete scaffold members 32 has a generally bead-shaped configuration. Each of the scaffold members 32 comprises a hydrogel encapsulating or containing a cell population, such as for example human mesenchymal stem cells. The media M is perfusable through the outer scaffold surface or interface and into an interior area or portion of the scaffold members 32, thereby permitting the inward diffusion of nutrients to the cells and outward diffusion of waste product by the cells. In one embodiment, the discrete scaffold members 32 are formed of alginate. In other embodiments, the discrete scaffold members 32 are formed from PCL or PLLA. Each of the discrete scaffold members 32 may have a diameter of between about 2 mm and about 4 mm.

In one implementation, the growth chamber 12 has a generally tubular configuration. The scaffold members 32 (e.g., alginate beads) encapsulating the cell populations are tightly packed within the tubular growth chamber 12, so that the scaffold members collectively have a generally tubular configuration and define an aggregated construct C, such as shown in FIG. 3.

Referring again to FIG. 2, media M moves through the inlet 18 and into the growth chamber 12 via pump 16, as shown by arrows X1. The media M is then moved through the pores and around the scaffold members 32, as shown by arrows X2, and then exits the growth chamber 12 through the outlet 20, as shown by arrows X3. The media M is movable through the growth chamber 12 at a selected flow rate, such as between about 0.1 mL/minute and about 47.0 mL/minute. In one implementation, the media M is movable through the growth chamber 12 at a flow rate of at least about 10 mL/minute, such as between about 20 mL/minute and about 40 mL/minute. Depending on the flow rate and the composition of the media M, the media M imparts shear stresses of between about 0.5 dynes/cm$^2$ and about 3.0 dynes/cm$^2$ proximate to surfaces of the discrete scaffold members 32.

The cell populations within the scaffold members 32 are thereby cultured as the media M is circulated through the growth chamber. The entire bioreactor system 10 may be stored in a cell culture incubator and easily transported to a cell culture hood.

In one implementation, the scaffold members 32 (e.g., the alginate beads) may then be dissolved away, leaving only the cultured cell populations, which define or form an extracellular matrix or aggregated construct. Thus, the remaining cell construct provides for a "scaffold-less" approach for engineering tissue. The cells are thus cultured in smaller beads or scaffold members 32, and then joined to form a single, mechanically intact relatively large construct.

In another implementation, the scaffold members (e.g. the alginate beads) are aggregated together to form a single large construct. Thus, the scaffold members and the encapsulated cells together define the construct, which may for example then be implanted into a defect site. Thus, the scaffold members (e.g. alginate hydrogel) may or may not be dissolved away depending on the particular application. Mechanical properties of the constructs, and the viability of the encapsulated cells, are demonstrated below.

The packed scaffold design in the growth chamber is based on the packed or fixed bed bioreactor sometimes used for the bulk production of recombinant proteins by mammalian cells. Portner et al. (2005) "*Bioreactor design for tissue engineering,*" J Biosci Bioeng 100:235; Meuwly et al. (2007) "*Packed-bed bioreactors for mammalian cell culture: bioprocess and biomedical applications,*" Biotechnol Adv 25:45. The tubular configuration of the growth chamber 12 design is sometimes used for the tissue engineering of vascular grafts, where vascular tissue growth is directed around the outside of a scaffold or the walls of a growth chamber. Williams et al. (2005) "*Perfusion bioreactor for small diameter tissue-engineered arteries,*" Tissue Eng 10:930; Williams et al. (2005) "*Endothelial cell-smooth muscle cell co-culture in a perfusion bioreactor system,*" Ann Biomed Eng 33:920; Huang et al. (2009) "*In vitro maturation of 'biotube' vascular grafts induced by a 2-day pulsatile flow loading,*" J Biomed Mater Res Part B Appl Biomater 91B:320; Engbers-Buijtenhuijs et al. (2006) "*Biological characterization of vascular grafts cultured in a bioreactor,*" Biomaterials 27:2390. However, the disclosed bioreactor systems differ from conventional perfusion systems, which provide for medium pumped directly through a porous scaffold sealed in a growth chamber. The disclosed systems also differ in design from conventional bioreactors used in vascular grafts, which typically provide for cell growth on the inside surface of an annular wall or within the wall itself. In the bioreactor system of the present invention, cell growth occurs inside and/or on a surface of the discrete scaffolds as opposed to outside a scaffold or along the growth chamber wall.

The "packed bead" approach of the present invention utilizes a collection of beads (or other discrete structures) as a scaffold construct, with the spaces between the beads as pores or channels of the construct. Thus, the disclosed system eliminates the need for a scaffold that precisely fits within a bioreactor chamber, such as in a conventional bioreactor chamber wherein fluid flow passes around the scaffold rather than through pores of the scaffold. In addition, the disclosed system eliminates the tendency for increased pressure drop during culture, such as prevalent in conventional bioreactors, given the spaces or pores between the beads remain relatively clear since the cells are largely entrapped within or on the surface of the beads. Further, the disclosed system allows for the "gluing" or adhering together of the beads (or other scaffold members) after culture, forming a single large engineered tissue or construct. The disclosed system also allows for the establishment of gradient culture environments along the length of the bioreactor growth chamber.

Thus, the disclosed systems may be used for the dynamic culture of any cell population and thus may be utilized in various tissue engineering applications, such as for example bone tissue engineering applications. In the TPS bioreactor, the medium is perfused through the growth chamber, exposing the cells to shear stress. Thus, an increased perfusion of nutrients into the scaffold is possible compared to conventional culture systems that focus on media mixing. Moreover, the disclosed systems avoid various technical difficulties, such as high pressure, scaffold interconnectivity requirements, and leaking that are associated with other prior systems.

In the disclosed systems of the present invention, the media flow through the growth chamber and around the tightly packed scaffolds enhances nutrient transfer while exposing the cells to shear stress. Results demonstrate that bioreactor culture supports early osteoblastic differentiation of hMSCs as shown by alkaline phosphatase gene expression. After 14 and 28 days of culture, significant increases in the gene expression levels of osteocalcin, osteopontin, and bone morphogenetic protein-2 (BMP-2) were observed with bioreactor culture, and expression of these markers was shown to increase with media flow rate. The results demonstrate the TPS bioreactor as an effective means to culture hMSCs and provide insight to the effect of long-term shear stresses on differentiating hMSCs. In particular, calcium deposition increased with shear, indicating that the stimulatory effects of the bioreactor culture were due in part to fluid shear stresses. The effects of both mass transport and shear stress on human bone marrow stromal cells were also evaluated by modifying the viscosity of the media. Cell growth and differentiation in the bioreactor system were enhanced by both mass transport and shear stresses.

The disclosed system also provides for a potential clinical application, given the alginate (or other suitable biomaterial) beads may be dissolved after extended culturing, leaving only cells and their extracellular matrix. Thus, a tissue engineering treatment option for bone, cartilage and skeletal muscle represents a promising alternative to current clinical options.

A central limitation to prior clinical options is the culture of three dimensional tissue engineering constructs in vitro. In static culture, nutrients and oxygen are replenished via diffusion. A nutrient gradient develops where cells on the exterior portions of scaffolds receive sufficient nutrients, while cells on the interior of scaffolds are deprived of nutrients and are exposed to hypoxic conditions. Malda et al. (2007) "*The roles of hypoxia in the In vitro engineering of tissues,*" Tissue Engineering 13:2153-62. For example, in a study analyzing oxygen concentration in three dimensional scaffolds, a preosteoblast cell line was seeded on demineralized bone matrix scaffolds at $5\times10^4$ cells/scaffold. Volkmer et al. (2008) "*Hypoxia in static and dynamic 3D culture systems for tissue engineering of bone,*" Tissue Engineering Part A 14:1331-40. These scaffolds were 9 mm in diameter and 5 mm in height and cultured in static and dynamic conditions. In static culture, central oxygen concentrations dropped quickly, below 10% in two days and to 0% in five days. Cell death was observed in areas where the central oxygen concentration was low. Dynamic culture in a bioreactor significantly improved oxygen transport, and although central oxygen concentrations dropped to 4%, cell death was not observed.

In the present bioreactor system, aggregated constructs were created as large as 6 mm in diameter and 30 mm in height, seeded at $3\times10^6$ cells/scaffold. Prior to scaffold aggregation, the individual alginate beads were cultured in the TPS bioreactor to enhance the growth of cells in the scaffolds. Following aggregation, the cells were no longer cultured in the TPS bioreactor, and were ready for implantation into a defect. By not attempting to culture such a large construct in vitro, the present method avoids nutrient transfer limitations, a major obstacle to three dimensional cell culture. Thus, an aggregated alginate scaffold may be created from many smaller cell containing scaffolds in a bioreactor system. The cells were viable throughout the scaffold as the constructs were rapidly fabricated.

Modular tissue engineering approaches had previously been attempted to create a perfusable cell containing construct (McGuigan et al. (2006) "*Vascularized organoid engineered by modular assembly enables blood perfusion,*" Proc Natl Acad Sci USA 103:11461-6), a cardiac sheet like construct (Leung et al. (2010) "*A modular approach to cardiac tissue engineering,*" Tissue Eng Part A 16:3207-18), and dermal equivalent tissue (Palmiero et al. (2010) "*Engineered dermal equivalent tissue in vitro by assembly of microtissue precursors,*" Acta Biomater 6:2548-53). However, such previous attempts relied either on cell aggregation or on a more complex approach such as tissue printing. In the present invention, a new approach is utilized whereby individual and discrete scaffolds (e.g., alginate beads) are assembled together prior to implantation. This approach creates a controlled aggregated construct within a bioreactor system quickly with relatively few fabrication steps.

The disclosed method for fabricating the aggregated scaffolds from alginate was developed following analysis of alginate bead dissolution curves in EDTA, where it was discovered that alginate beads first increase in diameter prior to dissolution. When using EDTA concentrations ranging from 0.008 M to 0.050 M, the initial expansion occurred over a sufficiently long period to manipulate beads prior to dissolution. The goal was to find an optimal EDTA concentration that could be used to form aggregated alginate constructs (AACs). Results indicated that dissolution in 0.025 M EDTA would be optimal as this concentration resulted in the largest initial increase in bead diameter. However, these dissolution curves may not be applicable to dissolution of alginate beads in other systems, given bead size can vary significantly due to swelling. For example, see Lee et al. (2000) "*Controlling mechanical and swelling properties of alginate hydrogels independently by cross-linker type and cross-linking density,*" Macromolecules 33:4291-4. This swelling results from ion exchange between the calcium crosslinking ions and monovalent ions in the environment of the bead. Bajpai et al. (2004) "*Investigation of swelling/degradation behaviour of alginate beads crosslinked with Ca2+ and Ba2+ ions,*" React Funct Polym 59:129-40; Moe et al. (1993) "*Swelling of Covalently Cross-Linked Alginate Gels—Influence of Ionic Solutes and Nonpolar-Solvents,*" Macromolecules 26:3589-97.

According to one embodiment, in order to fabricate the AACs, the alginate beads were tightly packed in the tubular growth chamber and were perfused with 0.025 M EDTA for 5 minutes to allow for expansion. EDTA is a chelator that sequesters the calcium ions used to crosslink alginate. When exposed to EDTA, alginate beads lose calcium ions, providing for free sites for crosslinking and the alginate beads start to swell as the alginate chains become more loosely crosslinked. Following this expansion, exterior edges of the beads overlapped with one another. Beads were then perfused with calcium chloride to ionically crosslink the overlapping edges, creating one aggregated construct from many beads. In particular, after exposure to EDTA, calcium ions are reintroduced, allowing for the crosslinking of alginate within and between beads to form the single construct.

In a study utilizing the TPS bioreactor, hMSCs were shown to express much higher levels of osteogenic markers osteocalcin and osteopontin than static controls. Yeatts et al. (2011) "*Tubular perfusion system for the long-term dynamic culture of human mesenchymal stem cells,*" Tissue Eng Part C Methods 17:337-48. In addition, mineralization was shown to be greatly increased throughout the bioreactor cultured beads. It was then determined if this mineralization would remain following AAC treatment by performing von Kossa staining for calcium. The stain revealed that hMSCs in the AACs had deposited calcium, and this calcium remained present throughout the AAC treatment. In vitro calcium deposition indicated that the hMSCs were able to differentiate into osteoblasts after 21 days and this calcium deposition remains present following AAC treatment.

Mechanical testing of AACs was then completed. Beads with various initial sizes were provided. Constructs composed of beads with initial diameters of 2.15 mm and 2.46 mm had significantly higher Young's Moduli, Ultimate Tensile Strength and Yield Strength compared to constructs composed of beads with initial diameters of 2.65 mm, 2.97 mm, and 3.90 mm. Young's modulus, Ultimate Tensile Strength, and Yield Strength all decreased with increasing bead size. It is believed that this occurs as beads with larger diameters are not able to pack as closely and create a less dense aggregated construct. Alginate compression testing has been previously reported in the literature. Kuo et al. (2001) "*Ionically crosslinked alginate hydrogels as scaffolds for tissue engineering: Part 1. Structure, gelation rate and mechanical properties,*" Biomaterials 22:511-21; Mancini et al. (1999) "*Mechanical properties of alginate gels: empirical characterization,*" J Food Eng 39:369-78.

Previous studies to determine the mechanical strength have shown large variations based upon the specific alginate polymer used; however, aggregated alginate constructs according to the present invention revealed tensile properties in the lower range of alginates tested and Young's Moduli similar to previously described results. Drury et al. (2004) "*The tensile properties of alginate hydrogels,*" Biomaterials 25:3187-99. This demonstrates that the disclosed aggregated constructs are of sufficient strength for the engineering of tissue such as cartilage (Yoon et al. (2008) "*Effects of exogenous IGF-1 delivery on the early expression of IGF-1 signaling molecules* by alginate embedded chondrocytes," Tissue Eng Part A 14:1263-73; Yoon et al. (2007) "*Effect of construct properties on encapsulated chondrocyte expression of insulin-like growth factor-1*," Biomaterials 28:299-306; Yoon et al. (2009) "*Addition of hyaluronic acid to alginate embedded chondrocytes interferes with insulin-like growth factor-1 signaling in vitro and in vivo*," Tissue Eng Part A 15:3449-59; Yoon et al. (2006) "*Chondrocyte signaling and artificial matrices for articular cartilage engineering*," Adv Exp Med Biol 585:67-86; Coates et al. (2010) "*Phenotypic variations in chondrocyte subpopulations and their response to in vitro culture and external stimuli*," Ann Biomed Eng 38:3371-88), non-load bearing bone (Abbah et al. (2008) "*Osteogenic behavior of alginate encapsulated bone marrow stromal cells: An in vitro study*," Journal of Materials Science-Materials in Medicine 19:2113-9), skeletal muscle (Rowley et al. (2002) "*Alginate type and RGD density control myoblast phenotype*," J Biomed Mater Res 60:217-23), and other tissues that may be engineered using alginate.

The accumulated alginate (or PCL, PLLA or other suitable biomaterial) constructs of the present invention provide an advantage over typical alginate constructs because individual alginate beads may be cultured in a bioreactor and then fabricated into one large construct. Thus, a relatively large construct may be created without nutrient transfer problems that occur in statically cultured large constructs. Indeed, given the utilization of numerous discrete scaffold members, there is virtually no limit on the size of the resulting construct that may be fabricated (comprising either "scaffold-less" aggregated cells, or comprising both aggregated scaffolds and cells) by the disclosed bioreactor system and method. For example, the fabrication of a construct having the gross size of a human femur (e.g., having a diameter of about 30 mm and a length of about 500 mm) or larger may be created according to systems and methods disclosed herein. Alternatively, a relatively small construct may be created, such as by utilizing fewer discrete scaffold members. Thus, the desired size of a construct is virtually unlimited. Moreover, metabolic activity assays indicate that the aggregated alginate construct treatment do not have a negative effect on the metabolic activity of cells (e.g., hMSCs) encapsulated in the alginate beads. Such a result was expected given the aggregated alginate construct treatment utilizes chemicals that are used in alginate bead fabrication and usage. This result was further confirmed by live dead staining, which indicated cells in aggregated alginate constructs were viable immediately and 24 hours after construct fabrication.

In one implementation, a clinical strategy for use of this construct is to first extract bone marrow from a patient, and isolate the mesenchymal stem cells. These stem cells are then encapsulated in alginate beads (or other discrete scaffold members), and then cultured in the TPS bioreactor. When the tissue is ready to be implanted into the defect site, the beads are aggregated in the bioreactor, removed, and then the construct is implanted into the patient. This will allow for the production of larger cell containing constructs compared to prior methods.

The results demonstrate that the disclosed construct may be easily fabricated, and has mechanical properties similar to or better than traditionally fabricated alginate scaffolds. The disclosed AAC thus has many potential applications, including non-load bearing bone, cartilage and skeletal muscle tissue engineering. By allowing cells to proliferate in smaller beads within the TPS bioreactor prior to aggregation, a large tissue engineering construct is created ready for implantation into a defect site.

An example experiment of a bioreactor system is provided:

Overview

Human mesenchymal stem cells (hMSCs) were cultured in individual alginate beads in a tubular perfusion system (TPS) bioreactor, and then aggregated to form a single large construct. Mechanical evaluation of the formed construct demonstrated that aggregated alginate constructs (AACs) made from beads with 2.15 mm diameters had a Young's modulus of 85.6±15.8 kPa, a tensile strength of 3.24±0.55 kPa and a yield strength of 1.44±0.27 kPa. These mechanical properties were shown to be dependent on the bead size used to fabricate the AACs, with smaller bead sizes resulting in stronger constructs. Analysis of metabolic activity revealed that hMSCs encapsulated in alginate exposed to AAC treatment sustained metabolic activity while live dead staining indicated cells remained viable. The results demonstrated the formation of AACs in the TPS bioreactor as an elegant method to create tissue engineering constructs in vitro.

Materials and Methods

Human Mesenchymal Stem Cell (hMSC) Culture hMSCs (p≤5) from a single donor were purchased from Lonza (Walkersville, Md.). Single donor cells were used to minimize variability associated with a primary cell population. Cells were cultured before the study in the control medium consisting of Dulbecco's Modified Eagle's Medium (Gibco of Carlsbad, Calif.) supplemented with 10% fetal bovine serum (Gibco), 1.0% v/v penicillin/streptomycin (Gibco), 0.1 mM nonessential amino acids (Gibco), and 4 mM L-glutamine (Gibco) using protocols set forth by the manufacture. See Betz et al. (2010) "*Macroporous hydrogels upregulate osteogenic signal expression and promote bone regeneration*," Biomacromolecules 11:1160; Chen et al. (2010) "*Macroporous hydrogel scaffolds and their characterization by optical coherence tomography*," Tissue Eng Part C Methods, 2010 Sep. 6 [Epub]. Cells were cultured on tissue culture polystyrene flasks with medium changes every 3 days according to the manufacture's specifications. Cells were stored in a cell culture incubator at 37° C. and 5% $CO_2$ and passaged every 6-7 days using trypsin/ethyldiaminetetraacetic acid (EDTA) (Lonza). The osteogenic medium was formulated as described in the literature by supplementing control media with 100 nM dexamethasone (Sigma, St. Louis, Mo.), 10 mM β-glycerophosphate, and 173 μM ascorbic acid (Sigma). Betz et al. (2010), supra, Biomacromolecules 11:1160; Chen et al. (2010), supra, Tissue Eng Part C Methods 2010 Sep. 6 [Epub]; Guo et al. (2008) "*Osteogenic differentiation of human mesenchymal stem cells on chargeable polymer-modified surfaces*," J Biomed Mater Res Part A 87A: 903.

Fabrication of Aggregated Alginate Constructs (AACs)

Alginate solutions of 2.0% w/v were prepared by adding alginic acid sodium salt from brown algae (Sigma, St. Louis, Mo.), into 0.15M NaCl (Sigma), and 0.025M HEPES (Sigma) in deionized water. Sikavitsas et al. (2003) "*Mineralized matrix deposition by marrow stromal osteoblasts in 3D perfusion culture increases with increasing fluid shear forces*," Proc Natl Acad Sci USA 100:14683; Sikavitsas et al. (2005) "*Flow perfusion enhances the calcified matrix deposition of marrow stromal cells in biodegradable nonwoven fiber mesh scaffolds*," Ann Biomed Eng 33:63; Stiehler et al. (2009) "*Effect of dynamic 3-D culture on proliferation, distribution, and osteogenic differentiation of human mesenchymal stem cells*," J Biomed Mater Res Part A 89A:96. Alginate beads were fabricated by dropwise addition of this solution into a stirred solution of 0.1 M calcium chloride (Sigma). The beads were stirred for 15 minutes using a magnetic stir bar and stir plate set to 60 rotations per minute. The beads were then removed from the calcium chloride solution and rinsed in a phosphate buffered saline (PBS) solution for 15 minutes. Bead size was varied by changing the needle gauge size. Gauges of 16, 18, 20, 27, and 30 were used. To make aggregated constructs beads were loaded into a growth chamber to make an aggregated construct approximately 2 cm in length. A 0.025M solution of ethyldiaminetetraacetic acid (EDTA) (Sigma) was flowed through the growth chamber at 1.8 mL/min for five minutes. Allowing the EDTA to flow through the growth chamber for five minutes permits all the beads to be in full contact with the EDTA solution, and causes the alginate beads to expand in size and overlap. Following this step, the EDTA solution was replaced with a 0.5 M solution of calcium chloride. This solution was flowed into the TPS for 5 minutes at 1.8 mL/min to remove EDTA, then perfused through the growth chamber at 10 mL/minute for 20 minutes to form aggregated constructs by ionically crosslinking the alginate chains with the calcium ions. The five minute calcium chloride step is important to wash all remaining EDTA, while the 20 minute calcium chloride step distributes calcium ions to all beads. Aggregated alginate constructs were then removed from the TPS bioreactor for experimentation.

Measurement of Tensile Mechanical Strength

Prior to mechanical testing the dimensions of the AACs were measured using calipers and the mass of the sample measured using an Ohaus Analytic Plus analytical balance. Constructs were placed using forceps into custom fit clamps attached to the clamps provided by the manufacture and the tensile strength measured using a Tensilon RTF-1310 mechanical tester outfitted with a 50N load cell and MSAT0002 materials testing software. The AAC samples were stretched with a constant crosshead speed of 1.0 mm/min, with the software constantly recording the stress and strain. The test ended with sample fracture. Young's modulus, tensile strength, and yield strength of the AACs were calculated. The Young's modulus was calculated as the slope of the initial linear portion of the stress-strain curve. The ultimate tensile strength was identified as the maximum stress reached by each sample. The tensile strength at 0.2% yield was calculated by locating the intersection of the stress-strain curve and a line with the Young's modulus slope at 0.2% strain offset.

Measuring Rate of Bead Dissolution

To determine the dissolution rates of beads in EDTA beads were fabricated as described previously in the methods using an 18 gauge needle. Initial bead size was then measured by calculating the cross sectional area using Image J software (NIH, Bethesda Md.) of a bead based on an image taken with an Axiovert 40 CFL with filter set 23, (Zeiss, Thornwood, N.Y.) equipped with a digital camera (Diagnostic Instruments 11.2 Color Mosaic, Sterling Heights, Mich.). Alginate beads were loaded into TPS growth chamber and perfused with EDTA with concentrations ranging from 0.008M to 0.1M at 1.8 mL/min. At each time point, five beads were removed from the bioreactor and photographed. Cross sectional areas were normalized to initial cross sectional areas to determine bead dissolution at each time point.

Bioreactor Design

The bioreactor system consists of a tubular growth chamber and medium reservoir connected via a tubing circuit (See FIGS. 1 and 2). The medium's flow was driven by an L/S Multichannel Pump System (Cole Parmer, Vernon Hills, Ill.) at 3 mL/min for short-term studies and at either 3 or 10 mL/min for the long-term study. The entire tubing circuit is partially assembled outside the hood and sterilized via autoclave. The circuit consists of platinum-cured silicone tubing (Cole Parmer) for all areas except the area that passes through the pump, which is composed of Pharmed BPT tubing (Cole Parmer) chosen for its high mechanical durability. Tubing is connected using silver ion-lined microbial-resistant tubing connectors (Cole Parmer) to reduce the risk of bacterial contamination. The growth chamber consists of a length of platinum-cured silicone tubing (Cole Parmer) with an inner diameter of 6.4 mm, an outer diameter of 11.2 mm, and a wall thickness of 2.4 mm. The platinum-cured silicone tubing was chosen for its low chemical leachability, minimal protein binding, and high gas permeability to allow for the easy exchange of carbon dioxide and oxygen. The growth chamber was 13 cm in length and was packed with 30 cell-seeded alginate beads using a sterile spatula. Growth chamber tubing connectors were modified by adding 60 mesh stainless steel screens (Fisher Scientific, Pittsburgh, Pa.) to restrict bead movement. After loading, the autoclaved tubing was fully assembled inside a cell culture hood and then placed in a cell culture incubator at 37° C. and 5% $CO_2$. Fifty milliliters of the osteogenic medium was loaded into separate 125 mL Erlenmeyer flasks for each growth chamber topped with rubber stoppers. The medium is withdrawn and replaced from the reservoir through two tubes that penetrate the stopper and changed every three days by moving the bioreactor into a sterile culture hood, removing the medium in the reservoir, and replacing it with a fresh medium. This provides for a change of 85% of the medium. Beads are removed from the bioreactor by moving the entire bioreactor system into the hood, disconnecting one tubing circuit and flushing beads out of the growth chamber with phosphate-buffered saline (PBS).

hMSC Encapsulation in Alginate

Alginate solutions were sterilized via sterile filtration. hMSCs were removed from tissue culture flasks using trypsin/EDTA and pelleted via centrifugation at 500×g for five minutes. The cell pellet was re-suspended in the alginate solution at a density of $1.25-2.5 \times 10^6$ cells/mL. The alginate cell solution was added drop wise through a 20 gauge needle into a stirred solution of 0.1 M calcium chloride (Sigma) which immediately crosslinked the alginate to form beads. Beads were allowed to stabilize for 15 minutes and cultured in six well plates in control media for 24 hours. Beads were loaded into bioreactor and cultured in control media for use in live dead staining and osteogenic media in order to differentiate the hMSCs into osteoblasts and determine if calcium is produced as measured using von Kossa staining Control media was used for live dead and metabolic activity assays to observe the growth process when cells are not differentiating. Media was changed every three days.

Experimental Setup

On study day zero, bioreactor groups were loaded into the bioreactor, whereas control groups were placed in the osteogenic or control medium. Control group cells were cultured in 5 mL of the medium at five beads per well for the duration of the study with medium changes every 3 days for all groups. For all groups, five beads were used for each replicate and three replicates were taken for each sample. In the TPS bioreactor, different experimental groups and time points were cultured in different growth chambers, whereas replicates were cultured in the same growth chamber. Short term proliferation and differentiation studies were conducted for 8 days with time points on days 1, 4, and 8. Cell count data were not taken on day 1, but was taken on day 12 to provide more extended cell proliferation data. For all short-term studies, a group consisting of hMSCs cultured in the TPS bioreactor at a 3 mL/min flow rate was compared to hMSCs cultured in alginate in static conditions in osteogenic and control media. For long-term studies, time points were taken at days 14 and 28 to evaluate late osteoblastic differentiation. Experimental groups consisted of hMSCs cultured in the bioreactor at both 3 and 10 mL/min flow rates. These groups were compared to a static osteogenic control to evaluate the effect of flow rate on late osteoblastic differentiation.

Metabolic Activity hMSCs were encapsulated in alginate beads at 100,000 cells per bead. After stabilizing for 24 hours in control media in static culture, beads were exposed to either 35 minutes of control media with FBS (control group), 5 minutes of 0.1 M calcium chloride, 5 minutes of 0.025 M EDTA, and 25 minutes of 0.5 M calcium chloride (AAC treatment group), or 35 minutes of 70% methanol (Sigma) (dead control group). Metabolic activity was then assessed using a dimethylthiazolyldiphenyltetrazolium bromide (MTT) based in vitro toxicology kit (Sigma) as previously described. Betz et al. (2008) "Cyclic acetal hydrogel system for bone marrow stromal cell encapsulation and osteodifferentiation," Journal of Biomedical Materials Research Part A 86A:662-70. Briefly 200 µL of 5 mg/mL of reconstituted MTT was added to each well with 2 mL of control media with 10% FBS. Beads were then incubated for 150 minutes to allow for the formation of formazan crystals. Crystals were dissolved in 2 mL of MTT solubilization solution (Sigma) and allowed to dissolve out of alginate beads overnight. 200 µL of supernatant was then transferred to a 96 well plate to record the optical density in triplicate at 570 nm using an M5 SpectraMax microplate reader (Molecular Devices, Sunnyvale, Calif.).

Mathematical Model of the TPS

To determine flow velocities and calculate shear stresses a 2D steady-state Navier-Stokes model of the TPS was developed using COMSOL Multiphysics Version 3.5 (COMSOL, Burlington, Mass.). Initial flow into the growth chamber was modeled assuming fully developed flow. Walls of alginate beads were modeled as no slip, and the medium was assumed to have a dynamic viscosity of 0.78 centipoise and a density of 0.993 g/cm. Bacabac et al. (2005) "Dynamic shear stress in parallel-plate flow chambers," J Biomech 38:159. Boundary shear stresses were calculated using the formula $\tau=\mu(\delta v/\delta y)$, where $\mu$ is the dynamic viscosity of the media, v is the velocity of fluid at the bead surface, and y is the height of the boundary layer. The Sherwood number was calculated according to the standard equation for forced convection around a solid sphere with a diffusion coefficient of $2.56\times10^{-9}$ m$^2$/s. Allen et al. (2003) "Formation of steady-state oxygen gradients in vitro—application to liver zonation," Biotechnol Bioeng 82:253; Truskey et al. (2004) "Transport Phenomena in Biological Systems," Upper Saddle River: Pearson Prentice Hall; Kurosawa et al. (1989) "Diffusivity in gel beads containing viable cells," Biotechnol Bioeng 34:926. Diffusion of oxygen through alginate scaffolds was calculated using a COMSOL model with an oxygen diffusion coefficient in the medium and alginate of $2.56\times10^{-9}$ and $2.08\times10^{-9}$ m$^2$/s, respectively. hMSC cell respiration was modeled using Michaelis-Menten kinetics with an oxygen consumption rate of 0.012 µmol/10$^6$ cells/h, and a saturation constant of 0.011 mol/m$^3$. Zhao et al. (2005) "Effects of oxygen transport on 3-D human mesenchymal stem cell metabolic activity in perfusion and static cultures: experiments and mathematical model," Biotechnol Prog 21:1269. For static culture medium, oxygen concentration was fixed at 0.21 mM at the medium-air interface, and oxygen transport was modeled through the well and the bead. Peng et al. (1996) "Determination of specific oxygen uptake rates in human hematopoietic cultures and implications for bioreactor design," Ann Biomed Eng 24: 373. The ratio of air interface to bead surface area in the static model was modeled to reflect the ratio that exists within in vitro culture. Based on the Sherwood number indicating convective transport dominates diffusive transport, the bioreactor beads were modeled as having a homogenous saturated oxygen concentration at the exterior. Boundary conditions in static culture model consisted of insulation at the three walls of the well plate and a fixed concentration of 0.21 mM at the medium-air interface. A continuity boundary was used for the alginate beads. All figures are shown at steady state.

hMSC Isolation from Beads

At each time point hMSCs were isolated from the beads by incubating the beads for 25 min at 37° C. in 4 mL 0.025-0.1 M EDTA (Sigma). The cell solution was placed in a 15 mL falcon tube and centrifuged at 8000 g for 8 min to form a cell pellet. The pellet was then resuspended in PBS.

DNA Quantification

DNA was extracted at each time point using the following procedure previously described in the literature. Betz et al. (2008) "Cyclic acetal hydrogel system for bone marrow stromal cell encapsulation and osteodifferentiation," J Biomed Mater Res Part A 86A:662. Isolated cell pellets were resuspended in 200 µL of PBS isolated using a DNeasy Tissue Kit (Qiagen of Valencia, Calif.) following standard protocols to produce 400 µL of eluate. Double stranded DNA was then quantified by mixing 100 µL of DNA eluate with 100 µL of diluted Quant-iT PicoGreen dsDNA reagent (Molecular Probes, Carlsbad, Calif.), incubating for 5 min in the dark and measuring fluorescence using an M5 SpectraMax plate reader (Molecular Devices, Sunnyvale, Calif.) with excitation/emission of 480/520 nm. All samples were preformed in triplicate (n=3).

Cell Counts hMSCs were isolated from beads. Cell samples were removed, mixed with trypan blue (Sigma), and counted on a standard hemocytometer. Four counts were made for each sample (n=4).

Live-Dead Assay

Cell viability was assessed using a live dead assay following standard protocols as described previously. Betz et al. (2008) "Cyclic acetal hydrogel system for bone marrow stromal cell encapsulation and osteodifferentiation," Journal of Biomedical Materials Research Part A 86A:662-70. Viability tests were completed on three groups. In the control group, cells were cultured in static culture in control media. In the AAC group, cells were cultured in the bioreactor at a 3 mL/min flow rate for 10 days. AACs were formed from bioreactor cultured beads and removed from the bioreactor. In the final group, the AAC was cultured in a static culture plate to determine if the hMSCs could remain viable for 24 hours. AACs were either soaked in PBS to remove FBS and media for 30 minutes or moved to six well plate for 24 hour culture. Control beads were also first soaked in PBS for 30 minutes to remove FBS and media. Beads and AACs were then placed in well plates and incubated in 2 µm ethidium homodimer and 4 nm calcein AM (Invitrogen of Carlsbad, Calif.) for thirty minutes. Fluorescent images were then taken using a fluorescent microscope (Axiovert 40 CFL with filter set 23, Zeiss, Thornwood, N.Y.) equipped with a digital camera (Diagnostic Instruments 11.2 Color Mosaic, Sterling Heights, Mich.). AACs cultured in well plate were removed 24 hours later and stained following the same procedures as other groups.

Quantitative Reverse Transcriptase Polymerase Chain Reaction

RNA was extracted using an RNeasy mini plus kit (Qiagen) following standard protocols. Isolated RNA was then reverse transcribed to cDNA using a High Capacity cDNA Archive Kit (Applied Biosystems, Foster City, Calif.). Expression of BMP-2 (TaqMan Assay ID: Hs00154192_m1), osteocalcin (OCN, Hs01587813_g1), OPN (Hs00960641_m1), and alkaline phosphatase (ALP, Hs00758162_m1) was analyzed with glyceraldehyde-3-phosphate dehydrogenase (Hs00960641_m1) as an endogenous control gene for all samples. Gene expression assays (Applied Biosystems) were combined with the cDNA to be analyzed and TaqMan PCR master mix (Applied Biosystems). The reaction was performed on a 7900HT real-time PCR System (Applied Biosystems) using thermal conditions of 2 min at 50° C., 10 min at 95° C., and 40 cycles of 15 s at 95° C. and 1 min at 60° C. The relative gene expression level of each target gene was then normalized to the mean of the glyceraldehyde-3-phosphate dehydrogenase in each group. For ALP, the day 1 control medium group was used as a calibrator; for OPN, OCN, and BMP-2, the day 14 osteogenic medium group was used as a calibrator. Fold change was calculated using the DDCT relative comparative method as described previously. Yoon et al. (2009) *"Addition of hyaluronic acid to alginate embedded chondrocytes interferes with insulin-like growth factor-1 signaling in vitro and in vivo,"* Tissue Eng Part A 15: 3449; Kim et al. (2009) *"Effect of initial cell seeding density on early osteogenic signal expression of rat bone marrow stromal cells cultured on crosslinked poly(propylene fumarate) disks,"* Biomacromolecules 10:1810. Samples were completed in triplicate and standard deviations are reported (n=3).

Histological Analysis

Experimental hMSCs were cultured in individual alginate beads in osteogenic media in the TPS bioreactor for 21 days. On day 21, alginate beads were aggregated into AACs and were collected and fixed in 4% paraformaldehyde (Sigma) and 0.1 M sodium cacodylate (Sigma) buffer containing 10 mM calcium chloride at pH 7.4 at 4° C. for 4 hours. Following fixation, the beads were placed in cassettes and washed with 0.1 M sodium cacodylate buffer and 10 mM calcium chloride at pH 7.4 at room temperature for 24 hours. The beads were then dehydrated for histological processing by ethanol washes followed by two Citrisolv (Fisher Scientific) washes. The samples were then embedded in paraffin (Fisher Scientific) and sectioned to 5 μm thickness sections and placed on glass slides. Sections were oven dried at 64° C. for 2 hours, deparaffinized in Citrisolv and rehydrated in ethanol. Von Kossa staining was performed using standard protocols to visualize mineralization with a Nuclear Fast Red (Poly Scientific, Bay Shore, N.Y.) counterstain.

Statistical Analysis

All samples were completed in triplicate (n=3). Data were analyzed using single-factor analysis of variance followed by Tukey's Multiple Comparison Test assuming normal data distribution with a confidence of 95% ($p<0.05$). Mean values of triplicates and standard deviation error bars are reported on each figure as well as relevant statistical relationships.

Results

Formation and Dissolution of Alginate Beads

Alginate beads were fabricated to consistently different sizes using needle gauges of 16, 18, 20, 27, and 30 (Table 1). By using a needle gauge of 30 an average bead diameter of 2.15±0.07 mm was obtained. Sixteen gauge needles resulted in average bead diameters of nearly twice this magnitude with an average diameter of 3.90±0.09 mm. Needles with gauges in between these two resulted in bead diameters inside this range with each gauge needle producing beads significantly different in diameter from all other gauges ($p<0.05$). Based on these results beads of discrete diameters can be fabricated using different needle sizes.

TABLE 1

Alginate bead cross sectional area. Data are reported as mean ± standard deviation. All groups are statistically different ($p < 0.05$).

| Needle Gauge | Bead Diameter (mm) |
|---|---|
| 16 | 3.90 ± 0.09 |
| 18 | 2.97 ± 0.02 |
| 20 | 2.65 ± 0.07 |
| 27 | 2.46 ± 0.06 |
| 30 | 2.15 ± 0.07 |

Dissolution curves of beads were then generated using 0.1 M, 0.05 M, 0.025 M, and 0.008 M concentrations of EDTA. This analysis was performed with 2.97 mm diameter beads. Results of bead dissolution experiments revealed that 0.008 M EDTA did not dissolve alginate beads over the thirty minute experiment (FIG. 5). Cross sectional area was shown to increase slightly over the time points. For groups dissolved in 0.025 and 0.050 M EDTA bead size initially increased, but then decreased over later time points until complete dissolution in the 0.05 M group and near complete dissolution in the 0.025 M group. The 0.025 M EDTA group increased to 127% of original bead diameter after 5 minutes before dissolving to 11% of original area after 30 minutes. The 0.05 M group increased to 108% its original diameter before completely dissolving after 30 minutes. The 0.100 M group was shown to completely dissolve in 10 minutes without an increase at the 5 minute time point. These observed results in 0.025 M and 0.05 M EDTA likely occur as EDTA decreases the crosslink density of the alginate, causing the bead to initially grow in size before the bead is dissolved.

Mechanical Properties of Aggregated Alginate Constructs

Figure 5A:
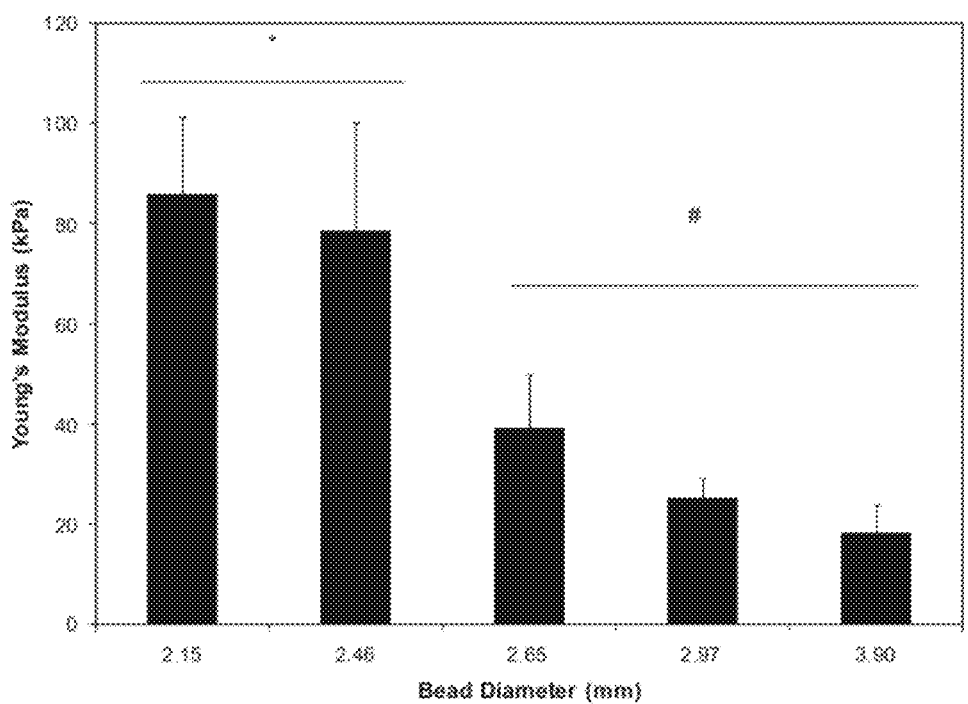

The initial increase in size of beads in the 0.025 M EDTA group was used to develop a protocol to make aggregated alginate constructs. Using this protocol these constructs were successfully created and shown to be easily transported and manipulated (FIG. 3). Mechanical testing of these constructs revealed that smaller diameter beads resulted in stronger aggregated constructs (FIGS. 5A, 5B, 5C). Aggregated constructs made from beads with 2.15 mm diameters had a Young's modulus of 85.6±15.8 kPa, a tensile strength of 3.24±0.55 kPa and a yield strength of 1.44±0.27 kPa. These values were statistically similar ($p>0.05$) to constructs made from beads with 2.46 mm diameter. Increase of bead diameter slightly to 2.65 mm resulted in a relatively large and statistically significant change ($p<0.05$) in mechanical properties producing constructs with a Young's modulus of 39.2±10.6 kPa, a tensile strength of 0.85±0.25 kPa and a yield strength of 0.52±0.15 kPa. These mechanical properties were statistically similar ($p>0.05$) to constructs made from beads with 2.97 mm and 3.90 mm diameters though beads with the largest diameter, 3.90 mm, exhibited the weakest mechanical properties. These samples had a Young's modulus of 18.2±5.6 kPa, a tensile strength of 0.45±0.04 kPa and a yield strength of 0.27±0.03 kPa. AAC fracture was typically observed on the periphery of beads aggregated together, however no other preferential breaking point was noted.

hMSC Viability and Calcium Deposition in Aggregated Alginate Constructs

Figure 7:
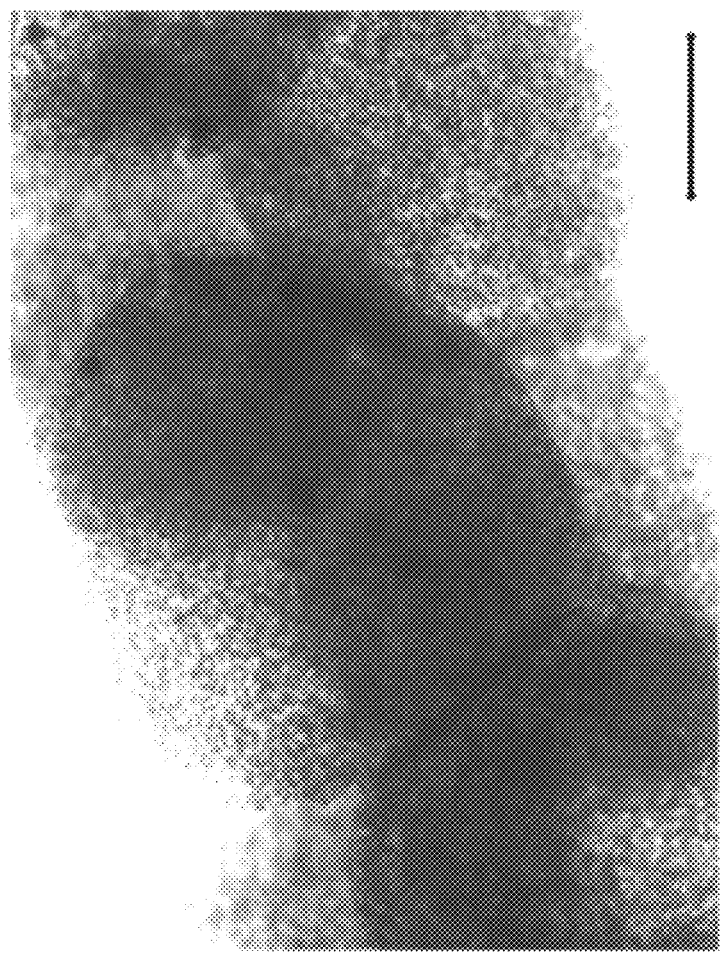
FIG. 7 is an exploded image of an AAC encapsulating cells, with a scale bar in the lower right corner representing 1000 μm. Cells are visible throughout the construct.
Figure 8:
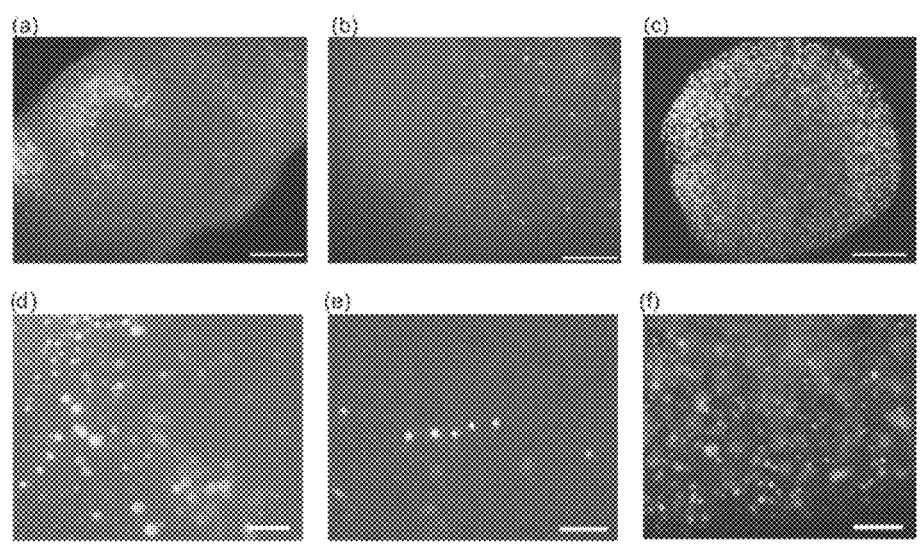
FIG. 8 (plates a, b, c, d, e, f) are live dead staining images of constructs and/or cells. Live dead strain of AAC after 10 days of individual bead TPS culture and formation is shown in plates (a) and (d). Live dead stain of AAC after 10 days of individual bead TPS culture and 24 hours of static culture following AAC treatment is shown in plates (b) and (e). Live dead staining of control after ten days of static culture is shown in plates (c) and (f). Cells appear viable in all groups. The scale bar in the lower right corner of plates (a), (b) and (c) represents 1000 μm. The scale bar in the lower right corner of plates (d), (e) and (f) represents 200 μm.

Results of MTT assay indicate AAC treatment has no effect on the metabolic activity of encapsulated hMSCs (FIG. 6). Cells in alginate beads exposed to AAC treatment had statistically similar metabolic activity to control hMSCs. Both these groups had significantly greater metabolic activity than hMSCs in beads exposed to methanol as a dead control. Microscopic images of the AAC reveal that hMSCs are homogenously distributed throughout the construct (FIG. 7). Upon live dead staining images reveal that the majority of these cells are viable after ten days of culture and AAC formation (FIG. 8). Live dead images of cells 24 hours after AAC treatment reveal that cells remain viable following the treatment. Following demonstration that hMSCs are viable in AACs, beads were cultured for 21 days in osteogenic media to demonstrate if calcium production was occurring as previously observed and if this calcium deposition would remain present throughout the AAC treatment. Images of AAC sections stained using von Kossa staining indicate that hMSCs produce calcium while being cultured prior to AAC formation and that AAC treatment does not eliminate these calcium deposits (FIG. 9). Calcium is stained black in these images and can be seen surrounding cells in AACs.

Functionality of Bioreactor System

Figure 10:
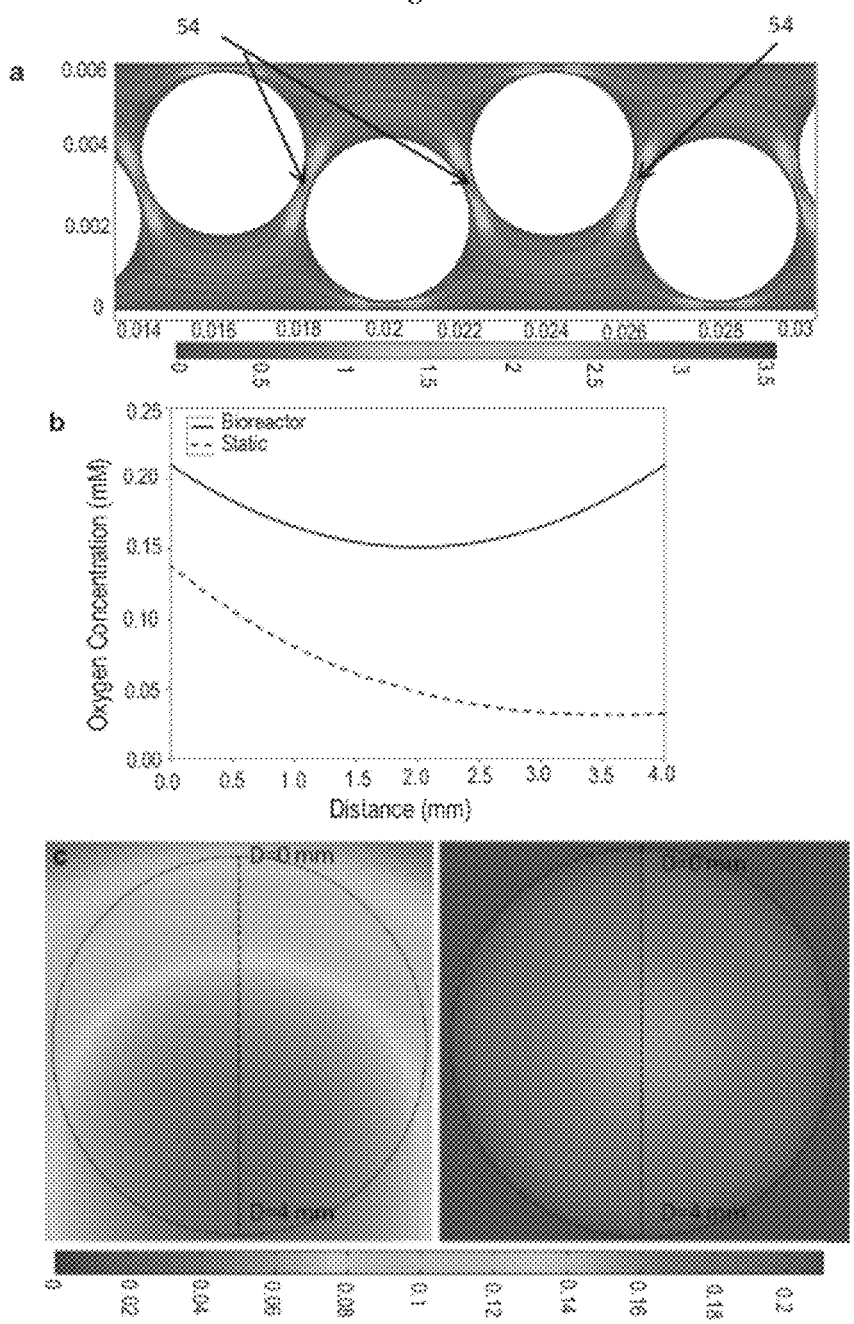
FIG. 10a illustrates a steady-state COMSOL model of the tubular perfusion system, with scaffold beads shown as white circles. Streamlines and grayscale map represent velocity in cm/s. The velocity ranged from approximately 0-1 cm/s except in the narrow regions or spaces (54) between adjacent beads, wherein the velocity in such narrow spaces was increased and ranged from approximately 1-3.5 cm/s. Dimensions of the growth chamber and beads are in meters. The model represents the middle section of the tubular perfusion system growth chamber with a 3 mL/min flow rate.
FIG. 10b illustrates graphically steady state oxygen concentrations throughout the alginate scaffold in static (--) and bioreactor (—) plotted along bead diameter. Concentrations of oxygen are plotted along the center of the scaffold from the inferior (D=0 mm) to the superior end (D=4 mm)
FIG. 10c is an overall image of bead diffusion model, with the dashed vertical line representing the cross section graphed in FIG. 10b. The grayscale map of FIG. 10c represents oxygen concentration in mM, with lower concentrations of between about 0-0.12 shown in the left plate of FIG. 10c and higher concentrations of between about 1.2-0.2 shown in the right plate of FIG. 10c.

Throughout all experimental trials the bioreactor system was shown to be free of leaks and contamination. The current system can accommodate multiple (e.g., 2, 3, 4 or more) independent tubing circuits and growth chambers. This allows for easy analysis of cells as one chamber can be removed without affecting the remaining chambers. Tubing connections were completed using silver ion-coated polyvinylidene fluoride fittings, which provide a secure yet highly customizable means to connect components of the system. The bioreactor system was quickly set up and scaffolds were easily removed for analysis. A 2D model of the growth chamber was completed and revealed the average shear stress at the bead surface to be $0.98 \pm 0.08$ dyn/cm$^2$ with a 3 mL/min flow rate and $2.98 \pm 0.22$ dyn/cm$^2$ with a 10 mL/min flow rate (FIG. 10a). To determine the effect of bioreactor culture on nutrient mass transfer the Sherwood number was calculated to be 22.71 and 13.34 with 10 and 3 mL/min flow rates, respectively, representing the ratio of convective to diffusive mass transfer. Diffusion models indicate that oxygen concentrations in the TPS bioreactor do not fall below 0.15 mM, whereas static cultured constructs fall to 0.03 mM (FIG. 10b). Oxygen concentrations in static cultured beads fall to the minimum at the farthest distance from the medium-air interface, whereas the homogeneity of the surrounding medium causes the bioreactor minimum concentration to occur at the center of the construct.

Short-Term Culture

Figure 11:
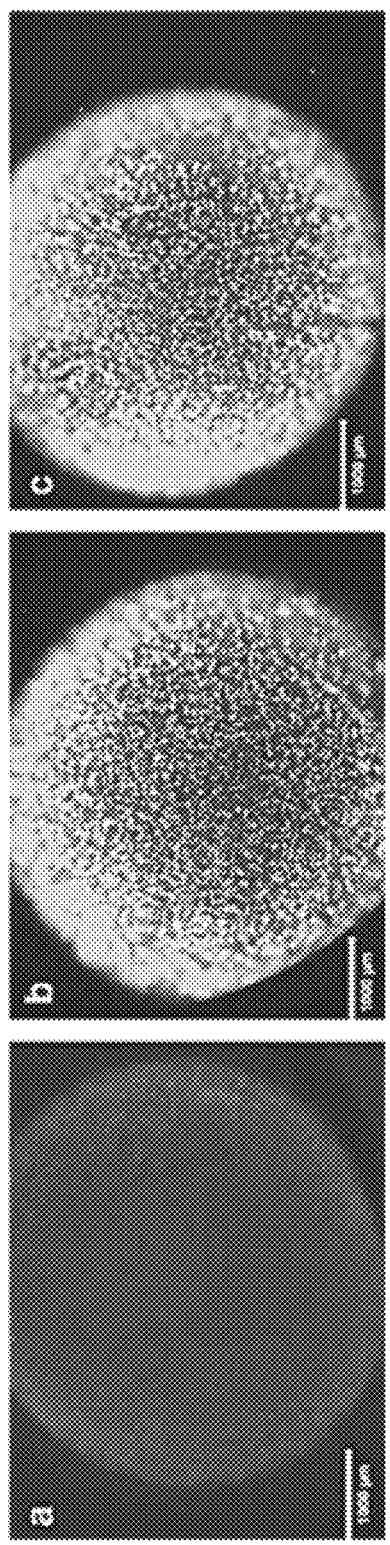
FIG. 11 (plates a, b and c) are live dead staining images of beads taken from day 8 of dead control (plate (a)), osteogenic control (plate (b)), and 3 mL/min flow bioreactor (plate (c)).
Figure 12:
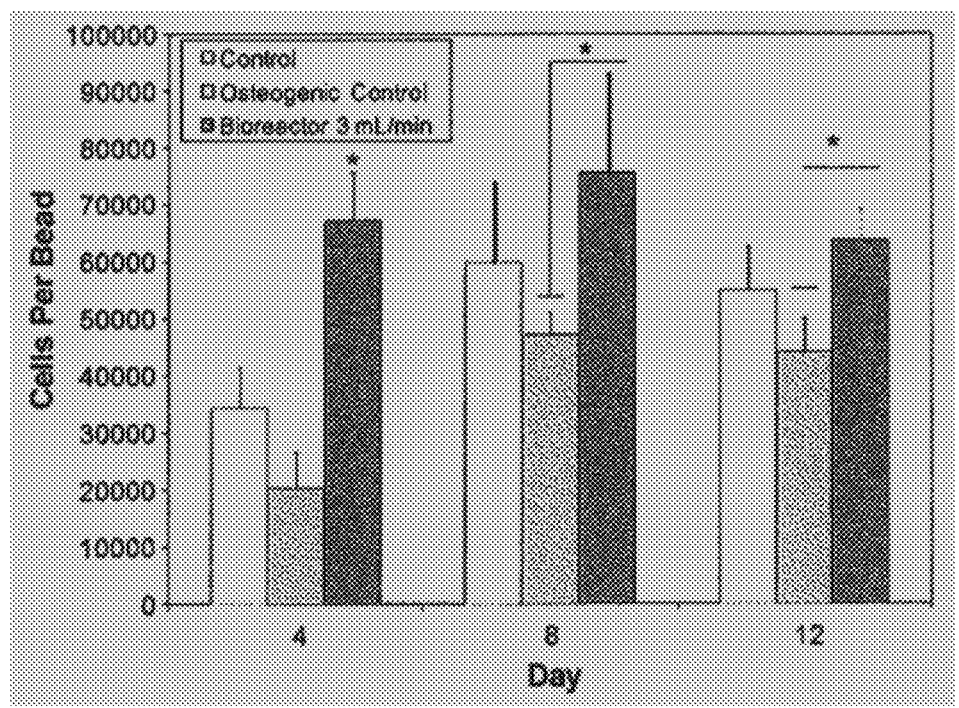
FIG. 12 illustrates graphically cell count data taken on days 4, 8 and 12 in static controls (osteogenic (middle bars in each group) and control (left bars in each group) media) and 3 mL/min flow in the bioreactor (right bars in each group). Cell counts indicate an elevated level of cells on days 4, 8 and 12 in the bioreactor compared to the control groups. Cells not cultured in the bioreactor show minimal proliferation over the study period. The symbol (*) indicates statistical significance within a time point ($p<0.05$).
Figure 13:
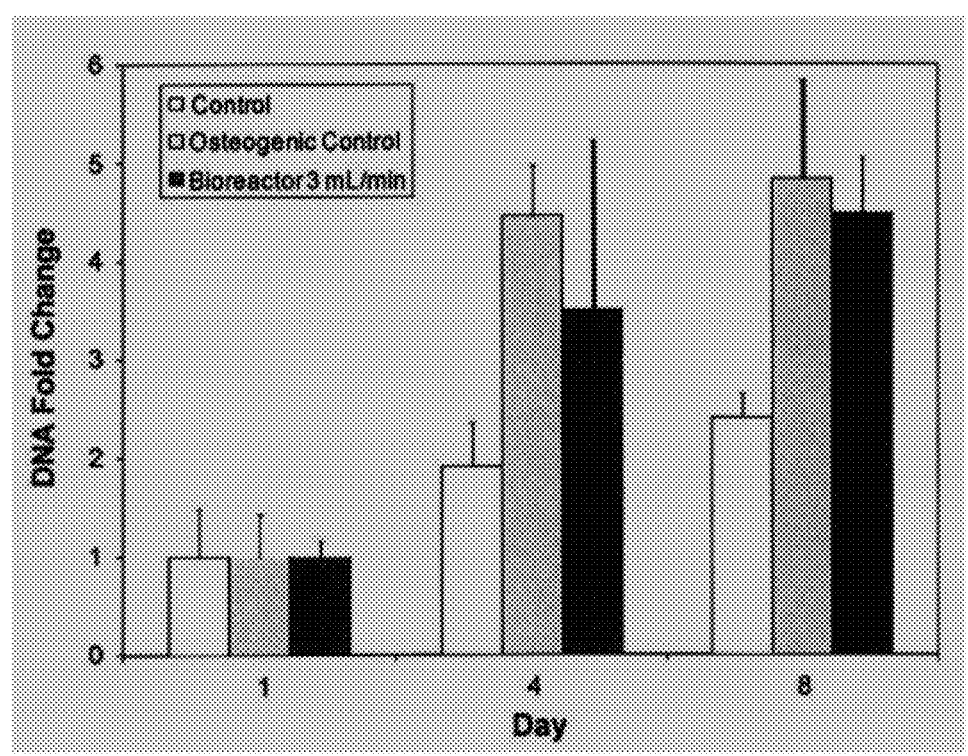
FIG. 13 illustrates graphically fold change of DNA content of cells in static control (left bars in each group), static osteogenic control (middle bars in each group), and bioreactor (3 mL/min) based on DNA quantification from dsDNA reagent (PicoGreen®). Fold changes are based on day 1 DNA amounts. DNA amount indicates cell proliferation in the bioreactor throughout study.

To demonstrate the effectiveness of the bioreactor system for short-term culture, alginate beads containing an encapsulated population of hMSCs were cultured for 8 days and live-dead images of the whole bead were obtained on day 8 (FIG. 11). Nearly all cells appeared viable. Cell count data showed a significant increase in cell growth in the bioreactor as compared to day 4 controls ($p<0.05$) (FIG. 12). Average day 4 cell number in the bioreactor beads was $67,300 \pm 8400$ cells/bead, whereas the osteogenic control only had $20,400 \pm 6100$ cells/bead. Significant increase in cell growth was also observed on days 8 and 12 as compared to the osteogenic control ($p<0.05$). DNA quantification indicated cell proliferation in the bioreactor throughout the study (FIG. 13). By day 8 the bioreactor group had increased $3.41 \pm 0.58$-fold from its day 1 population numbers, greater than that observed in the controls. This demonstrates the effectiveness of the TPS bioreactor at supporting cell growth.

Figure 14:
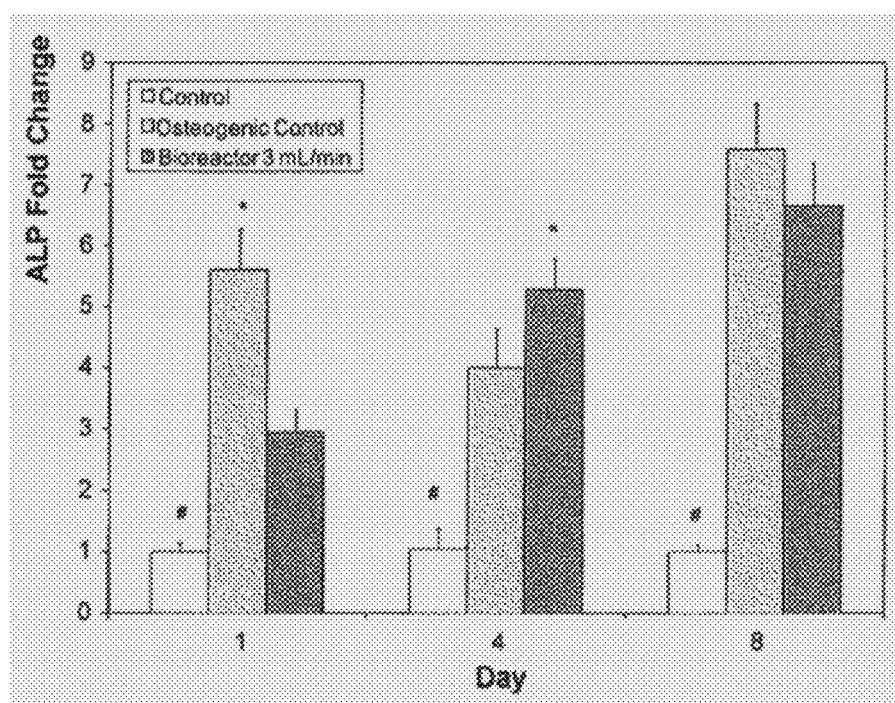
FIG. 14 illustrates graphically quantitative reverse transcriptase-polymerase chain reaction analysis after 1, 4 and 8 days for alkaline phosphatase (ALP), an early osteogenic marker. Static osteogenic control (middle bars in each group) and bioreactor (right bars in each group) are normalized to static control media samples. Results demonstrate higher day 1 expression of the osteogenic control as compared to the bioreactor on day 1, but greater expression on day 4 in the bioreactor group. Results indicate that the bioreactor system supports osteogenic differentiation of human mesenchymal stem cells. The symbols (*, #) indicate statistical significance within a time point ($p<0.05$).

Quantitative reverse transcriptase-polymerase chain reaction analysis was used to observe the gene expression of early osteogenic marker ALP on days 1, 4, and 8 (FIG. 14). Results indicate a significant increase of ALP mRNA expression as compared to static control medium bead on all days for both the static osteogenic control and the bioreactor flow group (3 mL/min), indicating that the hMSCs are undergoing osteogenic differentiation in both groups ($p<0.05$). On day 1, the static osteogenic group underwent a $5.6 \pm 0.7$-fold change in ALP expression as compared to the static control, whereas the bioreactor group underwent a $3.0 \pm 0.4$-fold change. By day 4 the bioreactor group showed a significantly higher $5.3 \pm 0.5$-fold day 4 expression increase compared to the $4.0 \pm 0.6$-fold increase of the static group ($p<0.05$). On day 8, the osteogenic group had a slightly elevated expression over the bioreactor group, a $7.6 \pm 0.7$-fold change compared to $6.7 \pm 0.7$-fold change. Results indicate that both bioreactor and static osteogenic groups are undergoing osteoblastic differentiation.

Long-Term Culture

Figure 15:
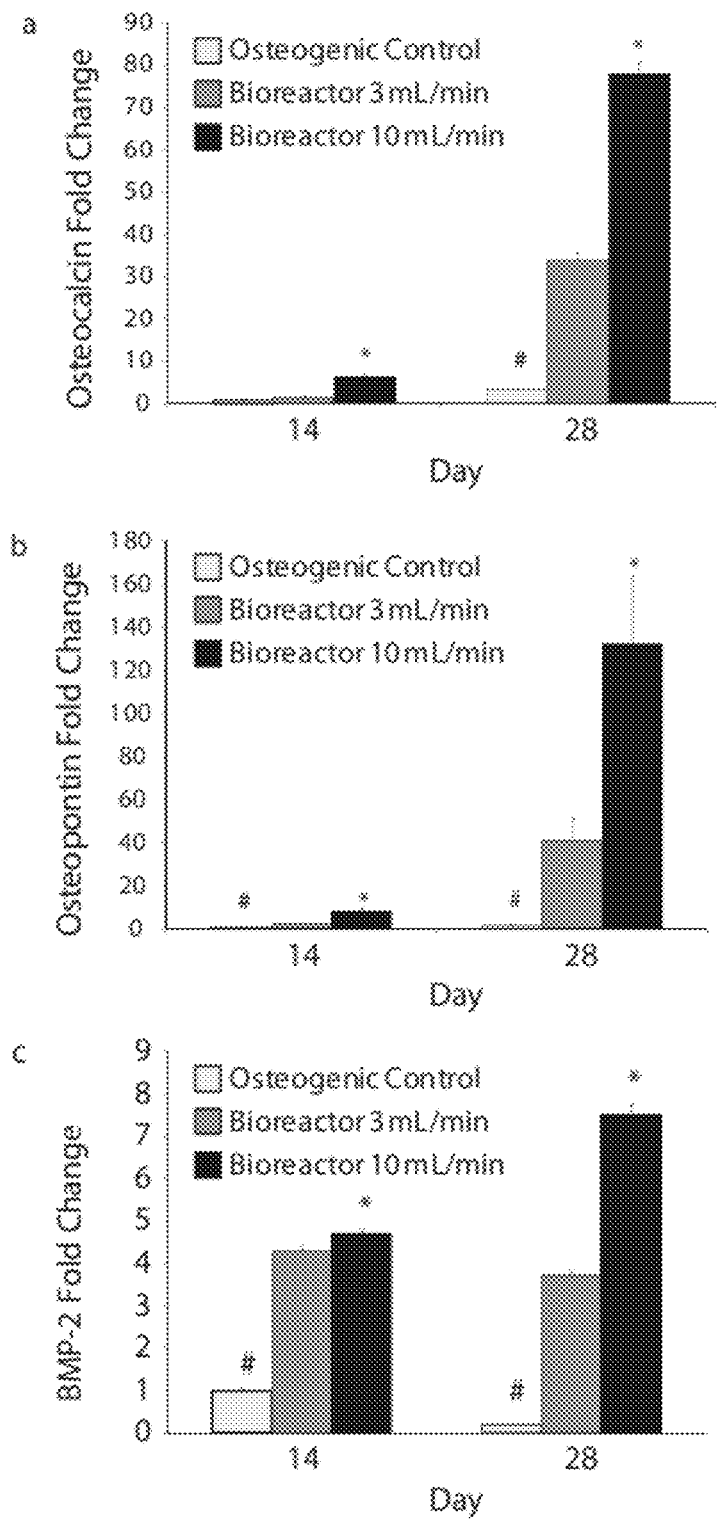
FIGS. 15a, 15b and 15c illustrate graphically quantitative reverse transcriptase-polymerase chain reaction analysis after 14 and 28 days for osteocalcin expression (shown in FIG. 15a), osteopontin expression (shown in FIG. 15b), and bone morphogenetic protein-2 (BMP-2) expression (shown in FIG. 15c). Data are normalized to day 14 static control. All groups were cultured using osteogenic media. Osteocalcin expression is significantly higher in 10 mL/min group than all other groups on day 14. On day 28, the 10 mL/min group has higher osteocalcin expression than the 3 mL/min group, and both groups show a significant increase over the static control (see FIG. 15a). Osteopontin expression is significantly higher in the bioreactor groups on days 14 and 28 as compared to the static control with the 10 mL/min group having the highest levels at both time points (see FIG. 15b). BMP-2 expression levels differ between all groups on both days 14 and 28 with the 10 mL/min group consistently having the highest expression level and the static control having the lowest (see FIG. 15c). The symbols (*, #) indicate statistical significance within a time point ($p<0.05$).

To determine the long-term effects of the bioreactor system, cells were cultured in alginate beads in the TPS bioreactor for 28 days. Two different flow rates were used, 3 and 10 mL/min, to evaluate the effect flow rate has on late osteoblastic differentiation. Reverse transcriptase-polymerase chain reaction analysis of BMP-2, OPN, and OCN was completed on days 14 and 28 (FIG. 15). Results demonstrate significantly increased expression of OCN for both bioreactor groups as compared to static osteogenic control on day 28 ($p<0.05$) (FIG. 15a). Similar expression of OCN was observed on day 14 for both static culture and the 3 mL/min flow rate group, but the 10 mL/min group showed a $6.2 \pm 0.7$-fold increase over the static group. On day 28, OCN expression levels increased $78.1 \pm 3.1$-fold as compared to the day 14 control, whereas the 3 mL/min group increased $34.1 \pm 1.7$-fold. The static group increased $3.3 \pm 0.3$-fold from days 14 to 28. This indicates that flow rate has a significant effect on late term osteoblastic differentiation with higher flow rates having a greater effect than lower flow rates. OPN gene expression data showed significant differences between all groups for both time points ($p<0.05$). On day 14 the 10 mL/min group had a $8.5 \pm 0.3$-fold expression change compared to the day 14 static control and the 3 mL/min group had a $2.5 \pm 0.6$-fold increase. On day 28 significant increases of $132.4 \pm 31.8$ and $41.2 \pm 10.5$-fold for the 10 and 3 mL/min groups, respectively, were observed. BMP-2 expression was also evaluated on both time points and shown to be elevated in all bioreactor groups as compared to the osteogenic control. BMP-2 expression also increased with increasing flow rate, as the 10 mL/min flow rate had higher BMP-2 expression levels for all time points. On day 28 BMP-2 shows approximately a twofold increase in the 10 mL/min group as compared to 3 mL/min, similar to the fold increase of OPN and OCN between those groups on day 28.

Figure 16:
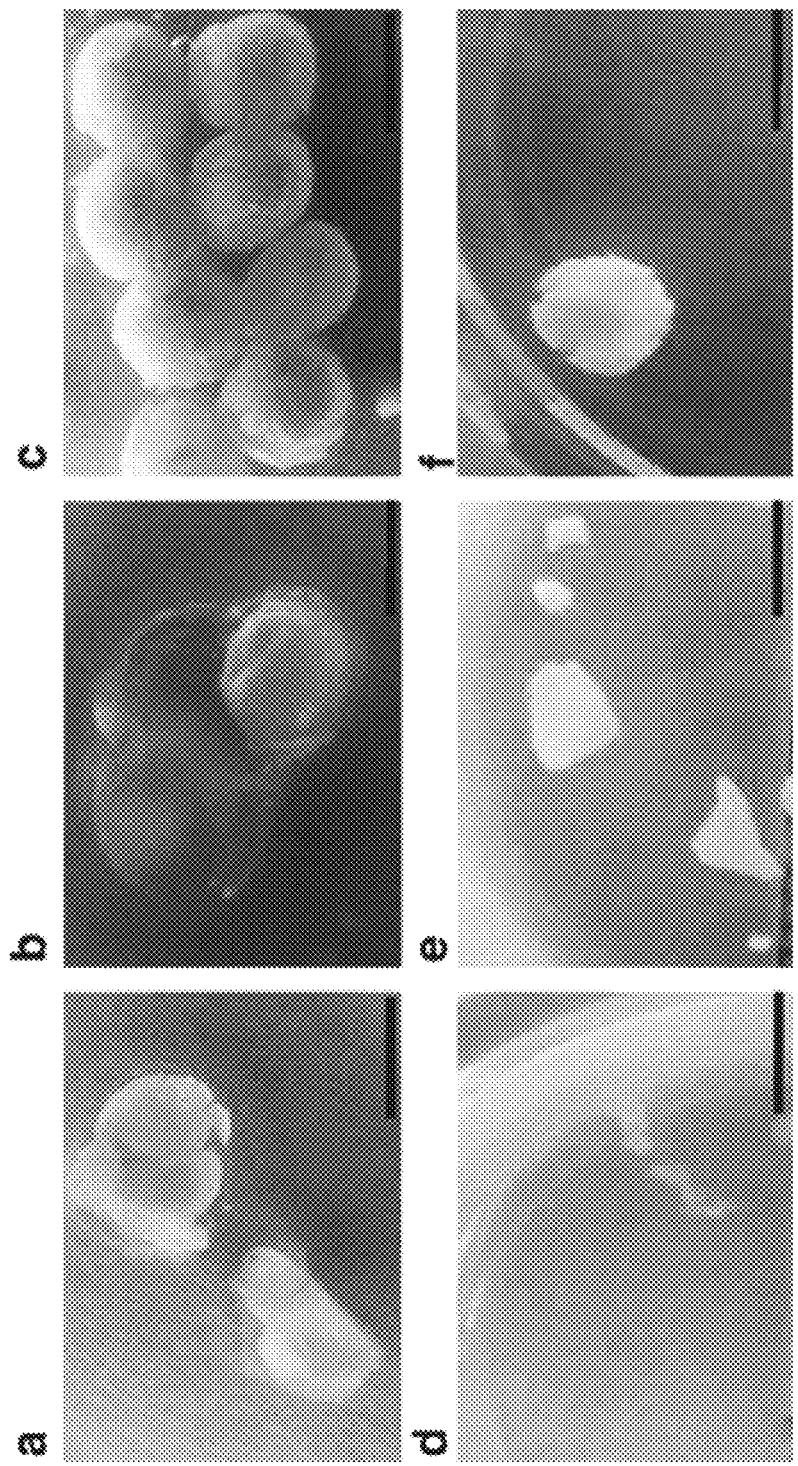
FIG. 16 (plates a, b, c, d, e and f) are images of scaffolds cultured for 28 days in static control media (plate (a)), static osteogenic media (plate (b)), and the bioreactor after 28 days of culture at 3 mL/min (plate (c)). Note that in the bioreactor group, white deposits can be seen on the surface of the scaffold, and the scaffold has maintained its shape. Static groups do not have white deposits and scaffold appears much less rigid.

To observe any macroscopic effects of bioreactor culture, images of the cell containing scaffolds were taken before analysis on day 28 (FIG. 16). White deposits can be seen on the surface of scaffolds removed from 3 mL/min bioreactor group (FIG. 16c). In the 10 mL/min flow group the cells scaffold construct largely dissolved before the final time point, indicating that the flow may be too high to sustain tissue formation. In the osteogenic control group minimal white deposits are observed and the scaffold appears less rigid, as the alginate dissolves over time (FIG. 16b). Alginate beads were then dissolved for 30 min in 0.025M EDTA and imaged. Photographs reveal that the alginate is completely dissolved in the control, leaving only small amounts of visible material (FIG. 16d). In the osteogenic control small fragments remain about 2 mm in diameter (FIG. 16e). In the 3 mL/min bioreactor group, larger, more intact structures are observed with diameters of about 4 mm (FIG. 16f).

Von Kossa staining was completed to observe calcium deposition in the scaffolds. Images of alginate beads on day 14 demonstrate that calcium deposition is restricted to the outside portion of the bead on day 14 (FIG. 17a-c). Calcium deposits appear to be in greater concentration in the 10 mL/min bioreactor group than in the osteogenic static group. Day 28 images reveal that mineralization is considerably higher in the 3 mL/min bioreactor group than in the static osteogenic group and static control group. Cells can be seen completely surrounded by a calcium matrix. The osteogenic control also has formed a mineralized matrix, but it appears to much less dense than the bioreactor group.

DISCUSSION

Using the disclosed bioreactor system, a tissue engineering bioreactor system was successfully designed and fabricated to create a facile method for the dynamic culture of hMSCs in 3D scaffolds. The TPS bioreactor has several key advantages over existing bioreactor systems. Many perfusion bioreactor systems are composed of customized components that require custom manufacture. Bancroft et al. (2003) "*Design of a flow perfusion bioreactor system for bone tissue-engineering applications,*" Tissue Eng 9:549; Grayson et al. (2008) "*Effects of initial seeding density and fluid perfusion rate on formation of tissue-engineered bone,*" Tissue Eng Part A 14: 1809; Janssen et al. (2006) "*A perfusion bioreactor system capable of producing clinically relevant volumes of tissue-engineered bone: in vivo bone formation showing proof of concept,*" Biomaterials 27:315; Cartmell et al. (2003) "*Effects of medium perfusion rate on cell-seeded three-dimensional bone constructs in vitro,*" Tissue Eng 9:1197; Porter et al. (2007) "*Noninvasive image analysis of 3D construct mineralization in a perfusion bioreactor,*" Biomaterials 28:2525.

The TPS bioreactor is composed entirely of off-the-shelf components, making the system easy to manufacture and modify. The TPS bioreactor is easily reproducible, allowing for more standardized experimentation and greater opportunity for clinical use, which would require consistency. The system may be easily modified to accommodate larger or smaller scaffold numbers and sizes through adjustment of growth chamber and medium reservoir size. The medium flow rate in this system may be accurately adjusted between about 0.16 and about 47.00 mL/min. This large flow rate range will allow for experimentation on the effect of flow rate on cell proliferation and differentiation. The bioreactor system is fully autoclavable to allow for easy sterilization. Bacterial contamination is a significant problem faced by perfusion bioreactor systems, and efficient sterilization will reduce this risk. Further, this sterilization method allows for easy reuse of tubing components.

Mathematical modeling revealed that the TPS bioreactor exposed the surface of the beads to shear stresses, and subsequent calculations indicated that mass transfer in the TPS bioreactor is dominated by convection rather than diffusion. Diffusion models indicated minimum oxygen concentrations to be over fivefold higher in bioreactor culture than in static culture. Oxygen concentrations similar to those calculated for static culture were shown to reduce the osteoblastic differentiation of rat osteoblasts. Oxygen concentrations in the TPS bioreactor remain high throughout the alginate constructs, as a homogenous oxygen concentration exists at the surface of the beads. Diffusion still dominates transport, which could result in low interior oxygen concentrations, especially if a different material or a higher cell seeding density is used. Bone growth requires aerobic growth conditions. The TPS bioreactor improves oxygen transport over static culture. As an example of the potential for hypoxic conditions, Volkmer et al. demonstrated that oxygen concentration in 9 mm static bone tissue engineering constructs dropped to 0% at the center of the scaffold and 4% at the edge of the scaffold after 5 days of static culture, indicating that diffusion is insufficient for oxygen transport. Perfusion culture was able to mitigate this effect. Volkmer et al. (2008) "*Hypoxia in static and dynamic 3D culture systems for tissue engineering of bone,*" Tissue Eng Part A 14:1331. Further increased flow in bioreactor systems has been shown to increase oxygen content in medium exiting the growth chamber. Thus, it is concluded that the TPS bioreactor both exposes the cell containing beads at the surface of the construct to shear stresses and provides for transport of oxygen and nutrients to cells in the scaffolds.

Further, the ability of the TPS bioreactor to support the growth and differentiation of hMSCs was demonstrated. The TPS bioreactor was shown to be effective in the culture of hMSCs. Over early time points bioreactor culture was shown to support proliferation of the cells. Bioreactor culture was shown to support osteogenic differentiation, but did not have a significant effect on mRNA expression of early osteoblastic marker ALP. This is consistent with bioreactor studies that report minimal effects of flow on ALP expression. Gomes et al. (2003) "*Effect of flow perfusion on the osteogenic differentiation of bone marrow stromal cells cultured on starch-based three-dimensional scaffolds,*" J Biomed Mater Res Part A 67A:87. Other studies report increased amounts of ALP expression with flow rate, indicating that specific parameters such as the shear stresses experienced by the cells could influence ALP expression. Bancroft et al. (2002) "*Fluid flow increases mineralized matrix deposition in 3D perfusion culture of marrow stromal osteoblasts in a dose-dependent manner,*" Proc Natl Acad Sci USA 99:12600; Stiehler et al. (2009) "*Effect of dynamic 3-D culture on proliferation, distribution, and osteogenic differentiation of human mesenchymal stem cells,*" J Biomed Mater Res Part A 89A:96. Based on the mathematical analysis, the average shear stresses at the surface of the beads in this study were 0.98±0.08 and 2.98±0.22 dyn/cm$^2$ for the 3 and 10 mL/min flow group, respectively. This model provides an estimate for surface shear stresses, with the following assumptions made in the creation of the model. First, it is assumed that all the alginate beads are substantially spherical in shape with a fixed diameter; however, in reality there may be minor observed variation between the exact size and shape of a bead. Second, the beads are stacked in an ideal manner in the model; however, there may be changes in the alignment of the beads in the TPS bioreactor. Finally, both the fluid flow and diffusion model are completed in two dimensions. Additional math models may be implemented to determine if fluid shears affect cells on the interior portions of the scaffold as current models focus on shear on the exterior surface of the bead. Fluid shear stresses of 1.6 dyn/cm$^2$ have been shown to upregulate OPN expression, whereas shear stresses of 12 and 20 dyn/cm$^2$ have been shown to increase ALP expression. Kreke et al. (2005) "*Fluid flow stimulates expression of osteopontin and bone sialoprotein by bone marrow stromal cells in a temporally dependent manner,*" Bone 36:1047; Grellier et al. (2009) "*Responsiveness of human bone marrow stromal cells to shear stress,*" J Tissue Eng Regen Med 3:302; Kapur et al. (2003) "*Fluid flow shear stress stimulates human osteoblast proliferation and differentiation through multiple interacting and competing signal transduction pathways,*" Bone 32:241. In long-term bioreactor culture, shear stresses of 0.15 dyn/cm$^2$ have been shown to increase OCN expression. Li et al. (2009) "*Effects of flow shear stress and mass transport on the construction of a large-scale tissue engineered bone in a perfusion bioreactor,*" Tissue Eng Part A 15:2773. Shear stresses in this system are in the range to enhance osteoblastic differentiation, but it is believed that in the TPS bioreactor, encapsulation of the hMSCs in the alginate leads to only a portion of the cell population being exposed to shear stresses as opposed to cells seeded on the surface of a porous scaffold. Thus, shear stresses may be too low to influence early osteoblastic differentiation, but high enough to affect late term differentiation and matrix deposition.

Further, the effects of flow rate on late osteoblastic differentiation and matrix production were evaluated. Expression of OCN and OPN, both late term markers of osteoblastic differentiation, was shown to be significantly upregulated in bioreactor culture as compared to a static osteogenic control. The 10 mL/min group showed higher expression of OCN than 3 mL/min group on day 14, indicating that 14 days are sufficient for the higher flow rate to begin influencing the osteoblastic differentiation. By day 28 both flow groups showed significant increases in expression as compared to the static control, with the 10 mL/min group having over a twofold increase in expression levels as compared to the 3 mL/min group. Similar results are seen in OPN signal expression levels. This result is significant as, though upregulation of late osteogenic markers has been previously demonstrated in perfusion bioreactors, our bioreactor uses a unique design in which cells are encapsulated in bulk scaffolds and the medium is not perfused directly through the pores of the scaffolds. Thus, it is noteworthy that such dramatic increases in late term osteogenic signals are observed.

Significant upregulation of BMP-2 was also observed during the long-term study in the bioreactor groups. BMP-2 is an early osteoblastic marker that has been shown to enhance stem cell differentiation and promote osteogenesis in a scaffold. Bessa et al. (2008) "Bone morphogenetic proteins in tissue engineering: the road from laboratory to clinic, part II (BMP delivery)," J Tissue Eng Regen Med 2:81; Bessa et al. (2008) "Bone morphogenetic proteins in tissue engineering: the road from the laboratory to the clinic, part I (basic concepts)," J Tissue Eng Regen Med 2:1; Betz et al. (2009) "Tissue response and orbital floor regeneration using cyclic acetal hydrogels," J Biomed Mater Res 90:819. As cells in the TPS bioreactor are already expressing high levels of late osteogenic markers, indicating terminal osteoblastic differentiation is occurring, the increased BMP-2 production observed with increasing flow may be effective in enhancing bone growth following implantation of the construct from the bioreactor system. Further investigation is necessary to completely elucidate the effect flow rate has on BMP-2 expression in this system and the effect this has on differentiation.

The clinical relevance of hMSCs cultured in alginate in the TPS bioreactor is twofold. First, the alginate beads could be removed from the bioreactor and directly implanted into bone defects that do not have a load-bearing requirement. For example, certain types of craniofacial bone fractures heal poorly due to lack of neighboring bone and patients often have reported long-term sequelae even after currently available treatments. Patel et al. (2010) "Cyclic acetal hydroxyapatite nanocomposites for orbital bone regeneration," Tissue Eng Part A 16:55; Folkestad et al. (1999) "Long-term sequelae after surgery for orbital floor fractures," Otolaryngol Head Neck Surg 120:914; Rinna et al. (2005) "Orbital floor restoration," J Craniofac Surg 16:968; Betz et al. (2010) "Challenges associated with regeneration of orbital floor bone," Tissue Eng Part B Rev 16:541. Second, the alginate beads cultured in the TPS bioreactor could be loaded into a load-bearing carrier scaffold after cultivation for implantation into loadbearing defects such as long bones. This carrier scaffold would be constructed of a hard synthetic material such as poly(propylene fumarate), could be fabricated using stereolithography, and would feature a hollow interior to load the beads. Kim et al. (2010) "Stereolithographic bone scaffold design parameters: osteogenic differentiation and signal expression," Tissue Eng Part B Rev 16:523. Alternatively, future work will investigate the use of cylindrical or spherical synthetic scaffolds in the system. It is thought that these scaffold materials would also function in the system. Alginate is used in the system as cells can easily be encapsulated, avoiding complications occurring with the loading of some large 3D synthetic scaffolds. The alginate can also be easily dissolved allowing for creation of tissue without the presence of a scaffold. This may provide for the production of a section of engineered tissue that could be extracted and implanted into a patient. Based on results, longer culture period would be required, but in images taken at day 28, macroscopic differences could be seen between static and flow cultured constructs. White nodules can be seen on the periphery of scaffolds removed from the bioreactor, whereas minimal formations were observed in static osteogenic control groups. After dissolution of the scaffold, extracellular matrix depositions of nearly the same size as the original cell-scaffold construct were observed in the bioreactor group. These depositions were larger and more intact than the osteogenic static control. Despite higher expression of osteogenic markers, the 10 mL/min flow rate was shown to be too high for successful long-term culture in the TPS bioreactor as much of the cell-scaffold construct broke apart before the final time point. This would indicate that though the 10 mL/min flow rate stimulated the osteoblastic differentiation of the cells, it was too high to support the macroscopic growth of tissue. Thus, an optimal flow rate of between 3 and 10 mL/min may be provided, in which matrix deposition is enhanced, but scaffold dissolution does not occur too quickly. Late term differentiation was confirmed by observing the production of calcium by completing von Kossa staining. Higher amounts of calcium deposits were observed throughout the scaffold in the bioreactor groups as compared to the controls. On day 28, uniform dense mineralization is observed, whereas day 14 mineralization appears to be restricted to the edges of the scaffold in all groups. The upregulation of late osteoblastic markers observed in tandem with macroscopic differences in bead appearance and von Kossa staining indicate significant differences in late osteoblastic differentiation between static and bioreactor cultured cells.

To enhance the clinical relevance of cell-based tissue engineering utilizing 3D scaffolds, in vitro culture techniques must be improved. The disclosed bioreactor systems effectively enhance the in vitro proliferation of hMSCs, and the differentiation of these cells into osteoblasts. The disclosed system may therefore be utilized to produce clinically relevant tissue amounts through extended in vitro culture. The disclosed findings reveal that dynamic culture supports proliferation of hMSCs and enhances late osteoblastic differentiation. The TPS bioreactor utilizes a unique design, allowing for an alternative way to dynamically and efficiently culture cells.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A bioreactor system, comprising:
a growth chamber including an inlet and an outlet, said growth chamber defining a cavity;
a media reservoir in fluid communication with said inlet;
a pump configured to perfuse a media from said media reservoir into said inlet and through said growth chamber; and
a plurality of discrete scaffold members disposed within said cavity, wherein said discrete scaffold members comprise a material selected from the group consisting of alginate, poly(caprolactone) (PCL), and poly(1-lactic acid) (PLLA), each of said scaffold members having a generally bead-shaped configuration and encapsulating a viable cell population, wherein outer surfaces of adjacent scaffold members are ionically cross-linked together so that said plurality of scaffold members collectively form an aggregated construct with spaces between said adjacent scaffold members defining pores throughout said aggregated construct, the media movable between and around the scaffold members through said pores and perfusable into said discrete scaffold members via said pump.

2. The bioreactor system of claim 1, further comprising a first screen proximate to said inlet and a second screen proximate to said outlet, said plurality of discrete scaffold members packed within said growth chamber and maintained between said first and second screens.

3. The bioreactor system of claim 1, wherein said pump is a peristaltic pump.

4. The bioreactor system of claim 1, wherein said cell population is human mesenchymal stem cells.

5. The bioreactor system of claim 1, wherein said discrete scaffold members comprise alginate beads.

6. The bioreactor system of claim 1, wherein the media is moving through said growth chamber via said pump at a flow rate of between about 0.1 mL/minute and about 47.0 mL/minute.

7. The bioreactor system of claim 6, wherein the media is moving through said growth chamber via said pump at a flow rate of at least about 10 mL/minute.

8. The bioreactor system of claim 6, wherein the media imparts shear stresses of between about 0.5 dynes/cm$^2$ and about 3.0 dynes/cm$^2$ proximate to surfaces of said discrete scaffold members.

9. The bioreactor system of claim 1, wherein each of said discrete scaffold members has a diameter of between about 2 mm and about 4 mm.

10. The bioreactor system of claim 1, wherein said growth chamber has a generally tubular configuration so that said plurality of discrete scaffold members collectively have a generally tubular configuration.

* * * * *